US005876939A

United States Patent [19]
Reed et al.

[11] Patent Number: 5,876,939
[45] Date of Patent: Mar. 2, 1999

[54] FAS ASSOCIATED PROTEINS

[75] Inventors: John C. Reed, Carlsbad; Takaaki Sato, San Diego, both of Calif.

[73] Assignee: La Jolla Cancer Research Foundation, La Jolla, Calif.

[21] Appl. No.: 858,311

[22] Filed: May 19, 1997

Related U.S. Application Data

[63] Continuation of Ser. No. 410,804, Mar. 27, 1995, Pat. No. 5,632,994, which is a continuation-in-part of Ser. No. 259,514, Jun. 14, 1994, Pat. No. 5,747,245.

[51] Int. Cl.$^6$ .............................. C12Q 1/68; G01N 33/53
[52] U.S. Cl. ............................... 435/6; 435/7.1; 435/7.2; 435/7.21; 436/501
[58] Field of Search .............................. 435/6, 7.1, 7.2, 435/7.21, 29, 69.1; 436/501

[56] References Cited

U.S. PATENT DOCUMENTS 5,674,734  10/1997  Leder et al. ........................ 435/252.3
5,750,653  5/1998   Chu et al. .............................. 530/350

FOREIGN PATENT DOCUMENTS

WO
96/40864A  12/1996  WIPO .............................. C12N 1/21

OTHER PUBLICATIONS

Itoh et al., The Polypeptide Encoded by the cDNA for Human Cell Surface Antigen Fas Can Mediate Apoptosis, *Cell* 66:233–43 (1991).

Maekawa et al., "Molecular Cloning of a Novel Protein–tyrosine Phosphatase Containing a Membrane–binding Domain and GLGF Repeats," *FEBS Lett.* 337:200–206 (1994).

Sugawara et al., "Suppression of Stress Protein GRP78 Introduction in Tumor B/C10ME Eliminates Resistance to Cell Mediated Cytotoxicity," *Cancer Res.* 53:6001–6005 (1993).

Sato et al., "FAP–1: A Protein Tyrosine Phosphatase That Associates with Fas," *Science* 268:411–415 (1995).

Yanagisawa et al., "The Molecular Interaction of Fas and FAP–1," *J. Biol. Chem.* 272:8539–8545 (1997).

Takahashi and Kataoka, "Development of Anticancer Drugs Targeted of Fas–mediated Apoptosis Signal," *Chem. Abstr.* 126:7 (180671w) (1997).

Zhang and Winoto, "A mouse Fas–associated Protein with Homology to the Human Mort1/FADD Protein is Essential for Fas–Induced Apoptosis," *Mol. Cell. Biol.* 16:2756–2763 (1996).

Kalpana and Goff, "Genetic Analysis of Homomeric Interactions of Human Immunodeficiency Virus Type 1 Integrase Using the Yeast Two–hybrid System," *Proc. Natl. Acad. Sci. USA.* 90:10593–10597 (1993).

(List continued on next page.)

*Primary Examiner*—Kenneth R. Horlick
*Attorney, Agent, or Firm*—Campbell & Flores LLP

[57] ABSTRACT

The present invention provides mammalian protein tyrosine phosphatases, human PTP-BAS type 4, human PTP-BAS type 5a and mouse PTP-BAS type 5b, each of which is a Fas-associated protein (FAP), nucleic acid molecules encoding a PTP-BAS type 4 or a PTP-BAS type 5 and antibodies specific for a PTP-BAS type 4 or for a PTP-BAS type 5. The invention also provides methods for identifying FAP's, which can associate with Fas and can modulate apoptosis. The invention also provides screening assays for identifying an agent that can effectively alter the association of a FAP with Fas and, therefore, can increase or decrease the level of apoptosis in a cell. The invention further provides methods of modulating apoptosis in a cell by introducing into the cell a nucleic acid molecule encoding a PTP-BAS or fragment of a PTP-BAS or an antisense nucleotide sequence, which is complementary to a portion of a nucleic acid molecule encoding a PTP-BAS. The invention also provides a method of using a reagent that can specifically bind to a FAP to diagnose a pathology that is characterized by an increased or decreased level of apoptosis in a cell. The invention also provides methods of modulating apoptosis in a cell by contacting the cell with an agent that effectively alters the association of a FAP and Fas in a cell or alters the activity of a FAP in a cell.

12 Claims, 15 Drawing Sheets

OTHER PUBLICATIONS

Holt et al., "Phospatidylinositol 3–Kinase Activation is Mediated by High–Affinity Interactions between Distinct Domains within the p110 and p85 Subunits," *Mol. Cell. Biol.* 14:42–49 (1994).

Keller and Manak, DNA Probes, Stockton Press, pp. 5–6 (1993).

Innis et al., PCR Protocols: Methods and Applications, Academic Press, pp. 9–10 (1990).

Suda and Nagata, "Purification and Characterization of the Fas–ligand that Induces Apoptosis," *J. Exp. Med.* 179:873–879 (1994).

Fields and Sternglanz, "The two–hybrid System: An Assay for Protein–Protein Interactions," *Trends. Genet.* 10:286–292 (1994).

Schulze–Osthoff et al., "Divergent Signalling via APO–1/Fas and the TNF Receptor, two Homologous Molecules Involved in Physiological Cell Death," *EMBO J.* 13:4587–4596 (1994).

Songyang et al., "Recognition of Unique Carboxyl–Terminal Motifs by Distinct PDZ Domains," *Science* 275:73–77 (1997).

Itoh and Nagata, "A Novel Protein Domain Required for Apoptosis," *J. Biol. Chemistry* 268:10932–10937 (1993).

Chinnaiyan et al., Cell 81, 505–512, 1995.

Tartaglia et al., Cell 74, 845–853, 1993.

Polylinker reading frame:
GAA TTC CCG GGG ATC CGT CGA CCT GCA G
EcoRI    SmaI    BamHI    SalI    PstI

Amino acid sequence of HFAP10

1279
HGSPSPSVISKATEKETFTDSNQSKTKKPGISDVTDYSDRGDSDMD

EATYSSSQDHQTPKQESSSSVNTSNKMNFKTFSSSPPKPGDIF<u>EVE</u>
         1383  (1384)
<u>LAKNDNSLGISVT *VLFDK*GGVNTSVRHGGIYVKAVIPQGAAESDG</u>

<u>RIHKGDRVLAVNGVSLEGATHKQAVETLRNTGQVVHLLLEKGQSPT</u>

<u>SKEHVPVTPQCTLSDQNAQGQGPEKVKKTTQVKDYSFVTEENTF<u>E</u></u>

<u>VKLFKNSSGLGFSFSREDNLIPEQINASIVRVKKLFPGQPAAESGKI</u>

<u>DVGDVILKVNGASLKGLSQQEVISALRGTAPEVFLLLCRPPPGVLP</u>

EIDTALLTPLQSPAQVLPNSSKDSSQPSCVEQSTSSDENEMSDKSK

KQCKSPSRRDSYSDSSGSGEDDLVTAPANISNSTWSSALHQTLSN

MVSQAQSHHEAPKSQEDTICTMFYYPQKIPNKPEFEDSNPSPLPPD

MAPGQSYQPQSESASSSSMDKYHIHHISEPTRQENWTPLKNDLENH

LEDFELEVELL<u>ITLIKSEKGSLGFTVTKGNQRIGCYVHDVIQDPAKSD</u>

<u>GRLKPGDRLIKVNDTDVTNMTHTDAVNLLRAASKTVRLVIGRVLEL</u>

<u>PRIPMLPHLLP<u>D</u></u> (1883)

FIG. 12

Nucleotide sequence of HFAP10

3835/1279

CATGGCAGCCCTTCCCCATCTGTAATATCCAAAGCCACCGAGAAAGA
GACTTTCACTGATAGTAACCAAAGCAAAACTAAAAAGCCAGGCATT
TCTGATGTAACTGATTACTCAGACCGTGGAGATTCAGACATGGATGA
AGCCACTTACTCCAGCAGTCAGGATCATCAAACACCAAAACAGGAA
TCTTCCTCTTCAGTGAATACATCCAACAAGATGAATTTTAAAACTTT
TTCTTCATCACCTCCTAAGCCTGGAGATATCTTT<u>GAGGTTGAACTGG</u>

4149/1383

<u>CTAAAAATGATAACAGCTTGGGGATAAGTGTCACG</u>*GTACTGTTTG*

4150/1384

*ACAAG*GGAGGTGTGAATACGAGTGTCAGACATGGTGGCATTTATGT
GAAAGCTGTTATTCCCCAGGGAGCAGCAGAGTCTGATGGTAGAATTC
ACAAAGGTGATCGCGTCCTAGCTGTCAATGGAGTTAGTCTAGAAGGA
GCCACCCATAAGCAAGCTGTGGAAACACTGAGAAATACAGGACAGG
TGGTTCATCTGTTATTAGAAAAGGGACAATCTCCAACATCTAAAGA
ACATGTCCCGGTAACCCCACAGTGTACCCTTTCAGATCAGAATGCCC
AAGGTCAAGGCCCAGAAAAAGTGAAGAAAACAACTCAGGTCAAAGA
CTACAGCTTTGTCACTGAAGAAAATACATTT<u>GAGGTAAAATTATTT</u>
<u>AAAAATAGCTCAGGTCTAGGATTCAGTTTTTCTCGAGAAGATAATCT</u>
<u>TATACCGGAGCAAATTAATGCCAGCATAGTAAGGGTTAAAAAGCTC</u>
<u>TTTCCTGGACAGCCAGCAGCAGAAAGTGGAAAAATTGATGTAGGAG</u>
<u>ATGTTATCTTGAAAGTGAATGGAGCCTCTTTGAAAGGACTATCTCAG</u>
<u>CAGGAAGTCATATCTGCTCTCAGGGGAACTGCTCCAGAAGTATTCTT</u>
<u>GCTTCTGCAGACCT</u>CCACCTGGTGTGCTACCGGAAATTGATACTG
CGCTTTTGACCCCACTTCAGTCTCCAGCACAAGTACTTCCAAACAGC
AGTAAAGACTCTTCTCAGCCATCATGTGTGGAGCAAAGCACCAGCTC
AGATGAAAATGAAATGTCAGACAAAGCAAAAAACAGTGCAAGTCC
CCATCCAGAAGAGACAGTTACAGTGACAGCAGTGGGAGTGGAGAAG
ATGACTTAGTGACAGCTCCAGCAAACATATCAAATTCGACCTGGAGT
TCAGCTTTGCATCAGACTCTAAGCAACATGGTATCACAGGCACAGAG
TCATCATGAAGCACCCAAGAGTCAAGAAGATACCATTTGTACCATG
TTTTACTATCCTCAGAAAATTCCCAATAAACCAGAGTTTGAGGACA
GTAATCCTTCCCCTCTACCACCGGATATGGCTCCTGGGCAGAGTTAT
CAACCCCAATCAGAATCTGCTTCCTCTAGTTCGATGGATAAGTATCA
TATACATCACATTTCTGAACCAACTAGACAAGAAACTGGACACCT
TTGAAAAATGACTTGGAAAATCACCTTGAAGACTTTGAACTGGAAG
TAGAACTCCT<u>CATTACCCTAATTAAATCAGAAAAAGGAAGCCTGGG</u>
<u>TTTTACAGTAACCAAAGGCAATCAGAGAATTGGTTGTTATGTTCATG</u>
<u>ATGTCATACAGGATCCAGCCAAAAGTGATGGAAGGCTAAAACCTGG</u>
<u>GGACCGGCTCATAAAGGTTAATGATACAGATGTTACTAATATGACTC</u>
<u>ATACAGATGCAGTTAATCTGCTCCGGGCTGCATCCAAAACAGTCAGA</u>
<u>TTAGTTATTGGACGAGTT</u>CTAGAATTACCCAGAATACCAATGTTGCC
TCATTTGCTACCG<u>GAC</u> (5649/1883)

FIG. 13

Amino acid sequence of HFAP20

1377
SLGISVT _VLFDK_GGVNTSVRHGGIYVKAVIPQGAAESDGRI
(1445)
HKGDRVLAVNGVSLEGATHKQAVETLRNTGQV *TDHYTNL*

*LQYLRRAKQCVNNISSH\**

FIG. 14

Nucleotide sequence of HFAP20

4129/1377                             4149/1383                   4150/1384
AGCTTGGGGATAAGTGTCACG_GTACTGTTTGACAAG_GGAGGTGTGAATACG

AGTGTCAGACATGGTGGCATTTATGTGAAAGCTGTTATTCCCCAGGGAGCAGC

AGAGTCTGATGGTAGAATTCACAAAGGTGATCGCGTCCTAGCTGTCAATGGA

GTTAGTCTAGAAGGAGCCACCCATAAGCAAGCTGTGGAAACACTGAGAAATA
                       4332/1445
CAGGACAG*GTAACAGATCATTATACCAACCTTTTACAGTACCTTAGA*

*AGAGCAAAACAATGTGTGAATAACATCAGTTCTCAT*TG*AGATCTCTA*

*AATTTGTCAGCTAATCAAGAAACCAAGCCTGATATATATAACCATCTGGGTT*
*GTTGATTTTTCCTTCCAAATTGAAATGCAAGTATTACAAGACATTTTTTACT*
*GAGGAAGCTGACTTTCTATGTCACATTTAACGTTACATTACCAAAGAGATCT*
*GATGGGGGAGGGATGGAAATTGCATTTTAAATTTGTTGTATAAACATCTCAT*
*TTCTAGTGGTTTTCACTCTTATTCTTTAGCCTTAACACAAAATTTATTTTGTT*
*GAAGTACATTTTGAGTTAGGGAGTTTAACCAAATTATCTATAATGGTCTTTG*
*GAGGAAAAAGTTGTTGTTTTGAGACAGGGTGTTGCTGTGAGGCCCAGGCTGGA*
*GTGCAGTGGCGCAATCACGGCTCACTGCAACCTTGACTTCCCAG[-------]C*
*CTGGCTAATTTTTATATTTTTAGTAGAGATGGGGCCTCACCATGTTGGCCAGG*
*CTGGTCTCCAACTTCTGACCTCAGGTGATCTGCCCACCTTGGCCTCCCAAAGT*
*GTTAGCCTTACCAGCATGAGCCACTCCACCTGGCCATTATCATACATTTCTA*
*ACATGTATTATATTTATAATAGATTCTTTTTAATCATTTATCTTTCTATACA*
*GAAATGTAATAAAAACTTGATTTTGGAACTTTCAACCCCTTGCTTTTGTTCC*
*TCTATTTTTTTTTTCCCGGAATTCC*

FIG. 15

Amino acid sequence of MFAP23

(1975)                         (2007) (2008)
RAAISAPRFTKANGLTSMEPSGQPALMPKNSFS*KARTKPFF*

*QVIAIFNNQCAYVSYQIDFIIKCSSDTC**

FIG. 16

Nucleotide sequence of MFAP23

(5923)
AGAGCTGCCATTTCTGCGCCAGGTTCACCAAAGCCAAC

GGCCTAACCAGCATGGAGCCTTCTGGACAGCCTGCACTCA
                                (6021) (6022)
TGCCCAAGAACTCCTTCTCCAAG*GCAAGAACAAAACCTT*

*TCTTTCAAGTCATAGCCATTTTTAATAACCAATGTGCTT*

*ATGTGTCATACCAAATAGATTTCATAATTAAATGCTCTT*

*CAGACACATGCTAACAGTAGGACTGCTCTGTGATGAACT*

*AACAGGTTTTGCTCACACTGCAG*

FIG. 17

FAS ASSOCIATED PROTEINS

This application is a continuation of application Ser. No. 08/410,804, filed Mar. 27, 1995, issued under U.S. Pat. No. 5,632,994, which is a CIP of application Ser. No. 08/259,514, filed Jun. 14, 1994 U.S. Pat. No. 5,747,245.

BACKGROUND OF THE INVENTION

1. Field of the Invention

This invention relates generally to the fields of molecular biology and molecular medicine and more specifically to the identification of proteins involved in programmed cell death and associations of these proteins.

2. Background Information

Programmed cell death is a physiological process that ensures homeostasis is maintained between cell production and cell turnover in essentially all self-renewing tissues. In many cases, characteristic morphological changes, termed "apoptosis," occur in a dying cell. Since similar changes occur in different types of dying cells, cell death appears to proceed through a common pathway in different cell types.

In addition to maintaining tissue homeostasis, apoptosis also occurs in response to a variety of external stimuli, including growth factor deprivation, alterations in calcium levels, free-radicals, cytologic lymphokines, infection by some viruses, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral infections, induction of apoptosis can figure prominently in the pathophysiology of the disease process.

Some of the proteins involved in programmed cell death have been identified and associations among some of these proteins have been described. However, the mechanisms by which these proteins mediate their activity remains unknown. The identification of the proteins involved in cell death and an understanding of the associations between these proteins can provide a means for manipulating the process of apoptosis in a cell and, therefore, selectively regulating the relative lifespan of a cell.

A cell surface protein known as Fas (also called APO-1 and CD95; hereinafter "Fas"), which is expressed on various types of human cells, including breast, colon, prostate and pancreatic cancer cells, can trigger apoptosis. Fas is a member of the tumor necrosis factor receptor (TNFR) family of proteins, which also includes, for example, the nerve growth factor receptor. These receptor proteins transduce extracellular signals into a cell and, as a result, can induce cell death or promote cell survival. However, the mechanism by which cell surface receptors such as Fas regulate cell death is not known.

Since Fas is present on the cell surface, its action likely is mediated by Fas binding to one or more intracellular proteins, which ultimately effect cell death. The identification of such intracellular proteins that can associate with Fas and, therefore, can be involved in apoptosis would allow for the manipulation of this association as a means to modulate apoptosis in a cell. Thus, a need exists to identify proteins that associate with Fas. The present invention satisfies this need and provides additional advantages as well.

SUMMARY OF THE INVENTION

The present invention provides Fas-associated proteins (FAP's), designated PTP-BAS type 4 and PTP-BAS type 5, which are alternatively spliced forms of a protein tyrosine phosphatase (PTPase) that was originally isolated from basophils (PTP-BAS). In addition, a subfamily of PTP-BAS type 5 proteins is disclosed, including a human PTP-BAS type 5a and a mouse PTP-BAS type 5b, which lack a catalytic phosphatase domain. The invention also provides nucleic acid molecules encoding a PTP-BAS type 4 or a PTP-BAS type 5, vectors containing these nucleic acid molecules and host cells containing the vectors. The invention also provides antibodies that can specifically bind to a PTP-BAS type 4 or to a PTP-BAS type 5.

The present invention also provides a screening assay useful for identifying agents that can effectively alter the association of a FAP such as a PTP-BAS with Fas. By altering the association of Fas and a FAP, an effective agent can increase or decrease the level of apoptosis in a cell. For example, an agent that effectively reduces or inhibits the association of Fas and a FAP can increase the level of apoptosis, whereas an agent that effectively increases the association of Fas and a FAP can decrease the level of apoptosis.

The invention further provides methods of increasing or decreasing the amount of a FAP in cell, which can modulate the level of apoptosis. For example, the amount of a FAP in a cell can be increased by introducing into the cell and expressing a nucleic acid sequence encoding the FAP. Increasing the amount of a FAP in a cell can render the cell relatively resistant to apoptosis. In addition, the amount of a FAP in a cell can be decreased by introducing into the cell and expressing an antisense nucleotide sequence, which is complementary to a portion of a nucleic acid molecule encoding the FAP. Also, a fragment of the FAP that lacks PTPase activity can be expressed in a cell and can act as a dominant inhibitor of the FAP, thereby decreasing FAP activity in the cell. Decreasing the amount or activity of a FAP in a cell can render the cell relatively sensitive to apoptosis.

The invention also provides methods of altering the activity of a FAP and, consequently, of Fas in a cell, wherein such increased or decreased activity of the FAP or of Fas can modulate the level of apoptosis in the cell. For example, the activity of a FAP in a cell can be increased by introducing into the cell and expressing a nucleic acid sequence encoding the FAP, whereby the expressed FAP has phosphatase activity. In addition, the activity of a FAP in a cell can be decreased by introducing into the cell and expressing an antisense nucleotide sequence, which is complementary to a portion of a nucleic acid molecule encoding the FAP, whereby the reduced expression of the FAP results in reduced PTPase activity in the cell.

The invention also provides methods for using a reagent that can specifically bind a FAP or a nucleotide sequence that can bind to a nucleic acid molecule encoding a FAP to diagnose a pathology that is characterized by an altered level of apoptosis due to an increased or decreased level of a FAP in a cell.

LexA fusion proteins were produced by inserting a cDNA encoding an open reading frame of the cytoplasmic domain of Fas (amino acids 191 to 335) into the Eco RI/Bam HI site in the polylinker, which is downstream of the nucleic acid sequence encoding LexA (LexA 202). Cloning was performed so as to maintain the open reading frame of LexA into the inserted sequence such that a LexA fusion protein is produced. The nucleic acid encoding the fusion protein was expressed from an alcohol dehydrogenase promotor (ADH-P) and terminates at the ADH termination site (ADH-term).

Figure 2:
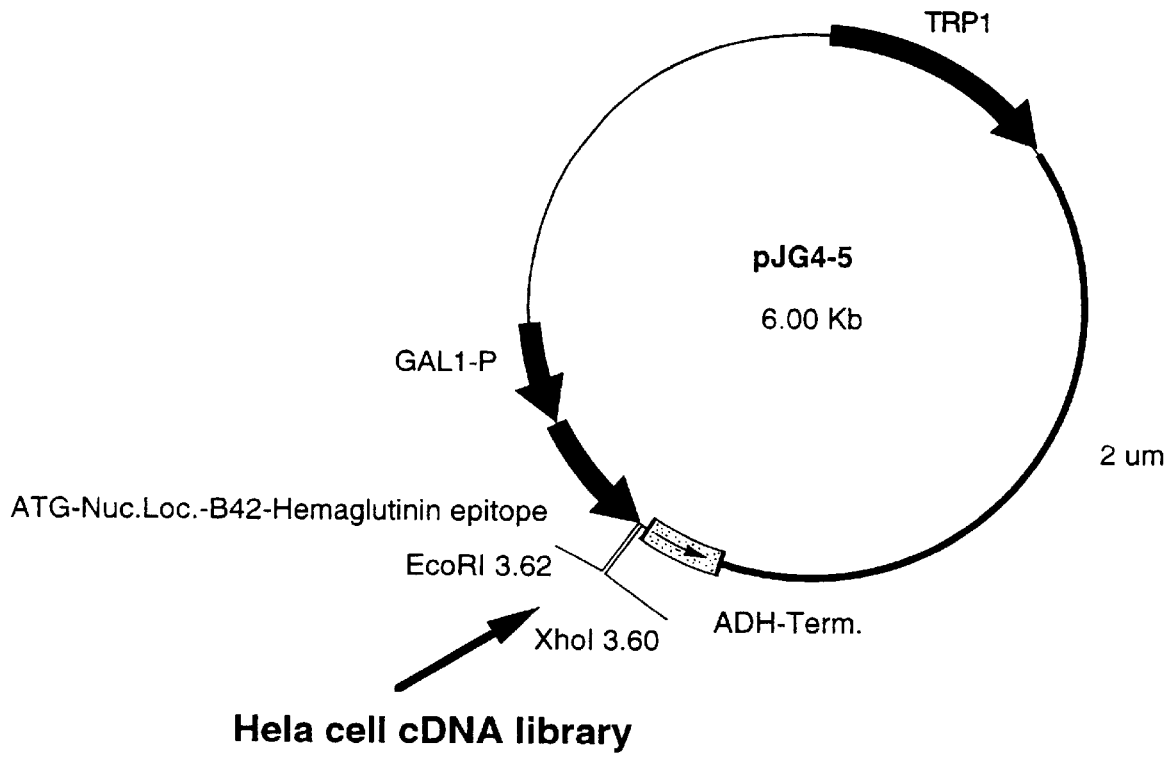

FIG. 2 provides a map of plasmid pJG4-5, which was used to produce B42 fusion proteins. The plasmid contains a 2 micron (2 μm) yeast origin of replication and a gene that allows a yeast cell containing the plasmid to grow in medium lacking tryptophan (TRP1). B42 fusion proteins were produced by inserting as shown HeLa cell-derived cDNA sequences, which can encode FAP's, into the Eco RI/Xho I sites located downstream of a cassette encoding an initiator methionine (ATG), an SV40 nuclear localization signal (Nuc. Loc.), the B42 trans-activator domain (B42) and a hemagglutinin HA1 epitope tag. The nucleic acid encoding the B42 fusion protein is expressed from a galactose-inducible promotor (GAL1-P). The plasmid also contain an ADH termination signal (ADH-term), which terminates transcription of the sequence encoding the fusion protein.

Figure 3:
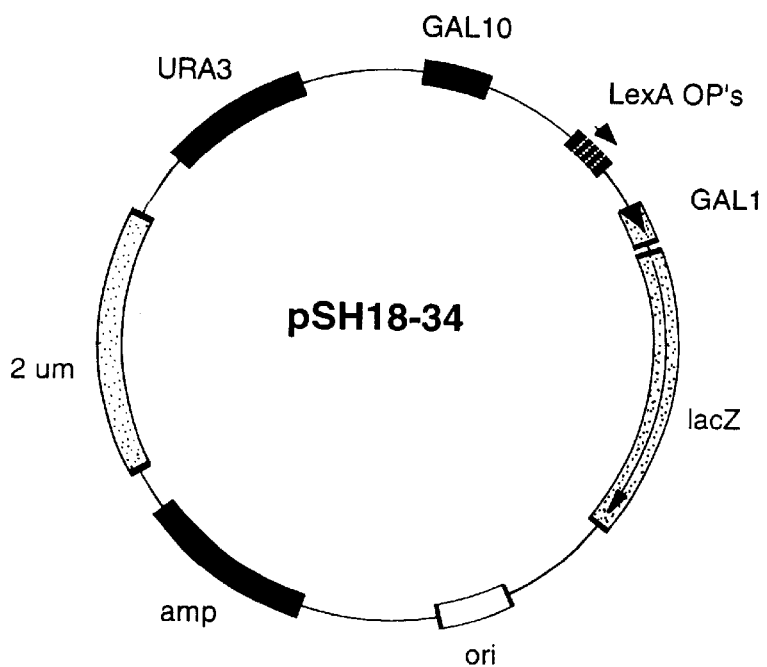

FIG. 3 provides a map of plasmid pSH18-34, which contains the reporter lacz gene encoding β-galactosidase (β-gal). The plasmid contains a bacterial origin of replication (ori) and an ampicillin resistance gene (amp). The plasmid also contains a yeast 2 micron (2 μm) origin of replication and a gene that allows a yeast cell containing the plasmid to grow in the absence of uracil (URA3). The lacZ gene is linked to a galactose-inducible promotor (GAL1). In addition to galactose, expression of the lacZ gene depends on LexA binding to the LexA operator sequences (LexA Op's) and trans-activation. pSH18-34 contains 8 LexA operators (LexA binding sites).

Figure 4:
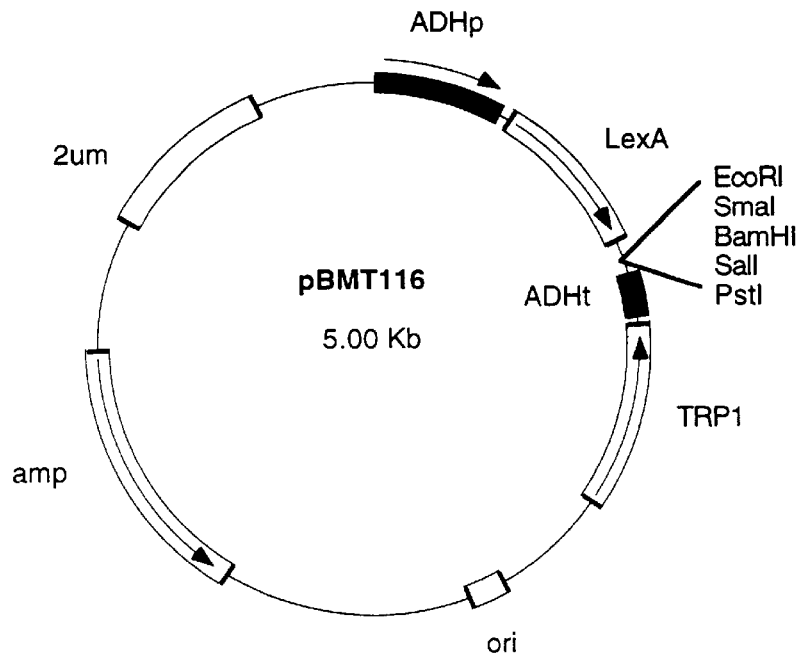

FIG. 4 provides a map of plasmid pBMT-116, which also was used to produce LexA/Fas fusion proteins. The plasmid contains a bacterial origin of replication (ori) and an ampicillin resistance gene (amp). The plasmid also contains a yeast 2 micron (2 μm) origin of replication and a gene that allows a yeast cell containing the plasmid to grow in the absence of tryptophan (TRP1). A LexA/Fas fusion protein was produced by inserting a nucleotide sequence encoding the cytoplasmic domain of Fas into the Eco RI/Bam HI sites located in the multiple cloning site. Cloning was performed so as to maintain the open reading frame of LexA into the inserted sequence such that a LexA/Fas fusion protein was produced.

Figure 5:
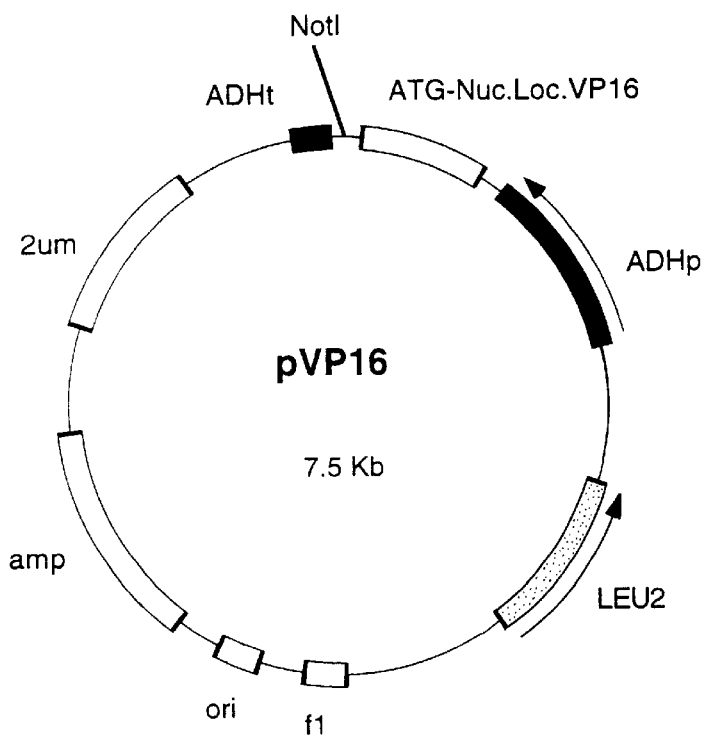

FIG. 5 provides a map of plasmid pVP-16, which was used to produce fusion proteins with the VP-16 transactivation domain. The plasmid contains a bacterial origin of replication (ori) and an ampicillin resistance gene (amp). f1 is a regulatory element that directs production of the antisense strand. The plasmid also contains a yeast 2 micron (2 μm) origin of replication and a gene that allows a yeast cell containing the plasmid to grow in the absence of leucine (LEU2). VP-16 fusion proteins were produced by inserting a cDNA library prepared from mouse embryo mRNA into the Not I restriction endonuclease site, which is downstream of the ATG start codon and VP-16 coding sequence (Nuc.Loc.VP16). Transcription is initiated from an ADH promotor (ADHp) and is terminated due to an ADH termination sequence (ADHt).

Figure 6:
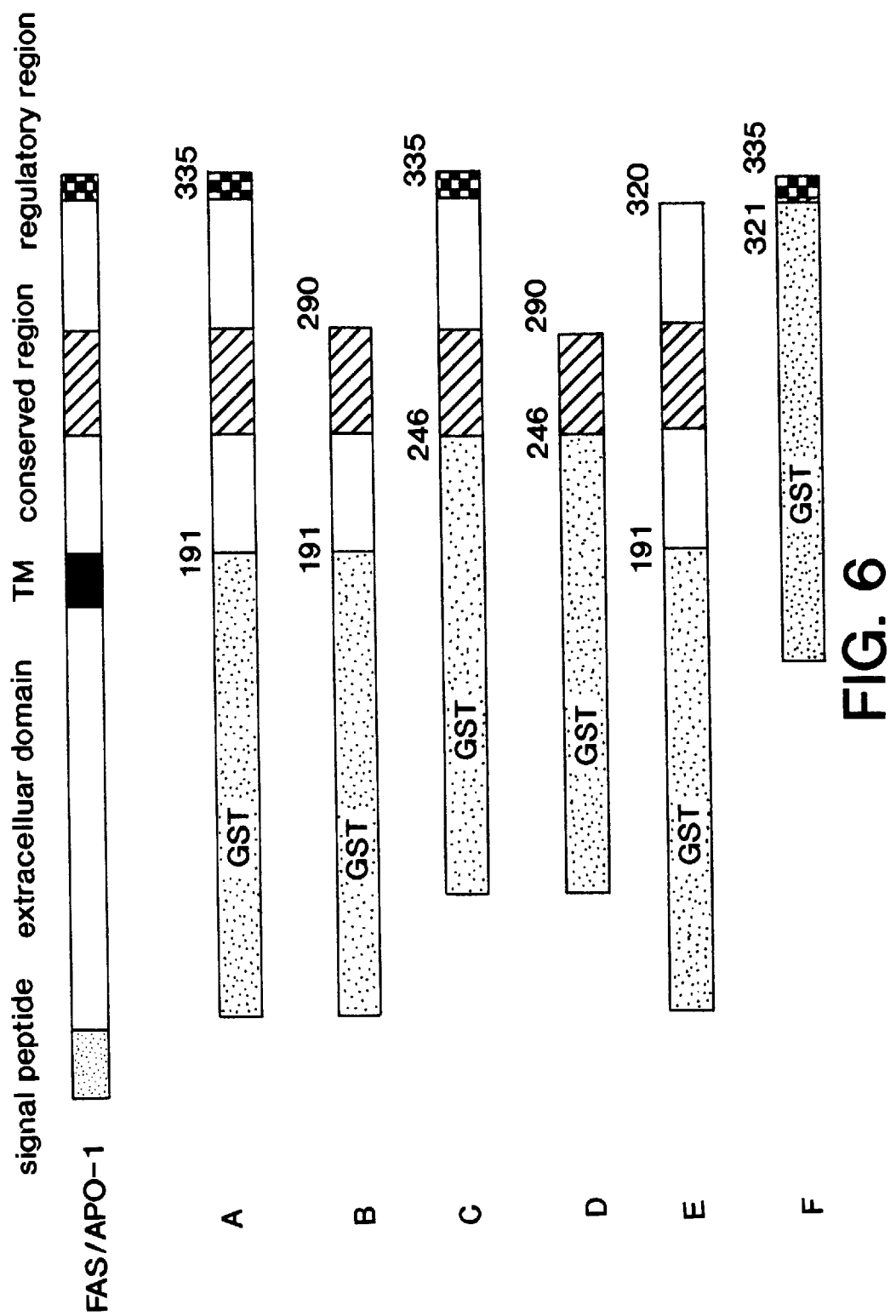

FIG. 6 schematically shows the Fas protein (FAS/APO-1) and various fusion proteins containing the glutathione-S-transferase protein (GST) linked to a fragment of Fas as follows: A) Fas(191–335); B) Fas(191–290); C) Fas(246–335); D) Fas(246–290); E) Fas(191–320) and F) Fas(321–335). TM indicates the transmembrane region of Fas. Numbers indicated the amino acid position relative to full length Fas protein.

Figure 7:
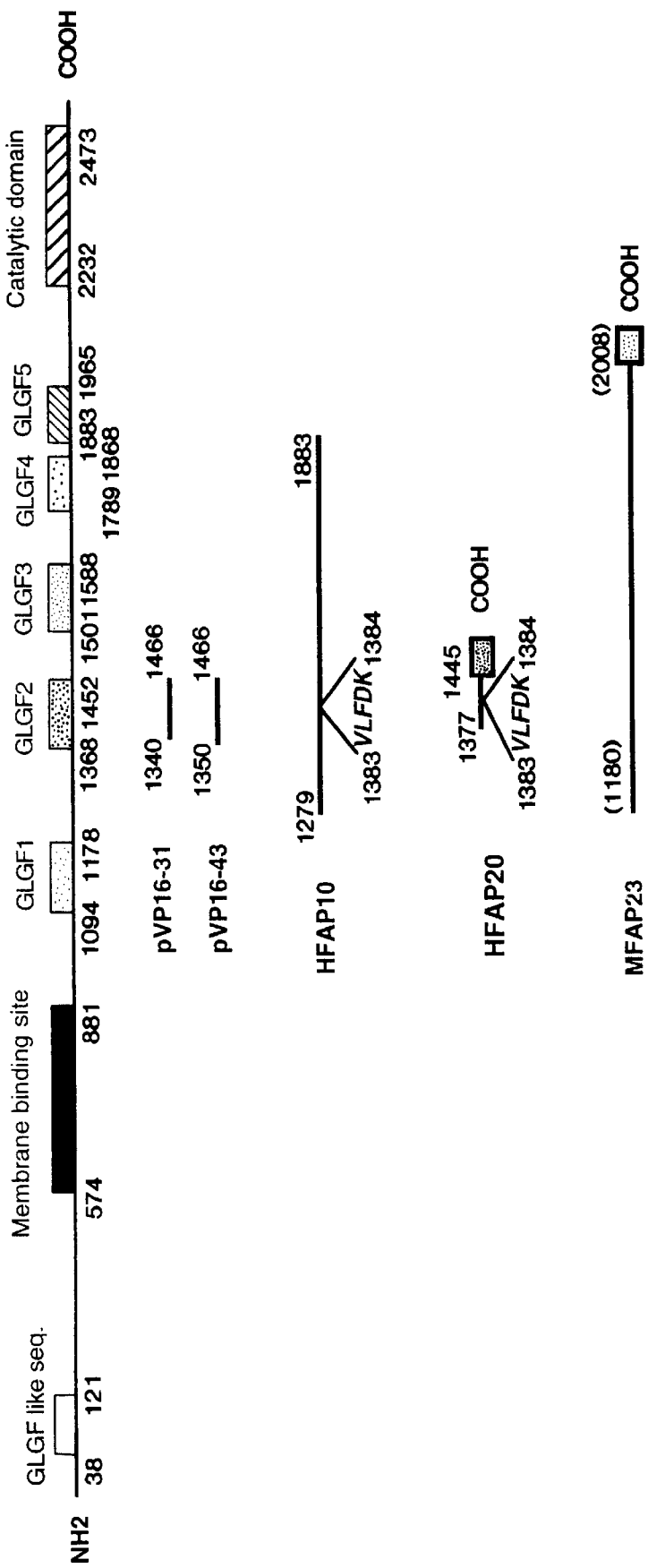

FIG. 7 schematically shows the PTP-BAS protein and indicates the conserved glycine-leucine-glycine-phenylalanine (GLGF SEQ ID NO:20) regions and the catalytic domain in the cytoplasmic domain of a PTP-BAS. Also shown are the homologous regions encoded by two cDNA clones obtained using the two hybrid assay (pVP16-31 and pVP16-43; see Example I), by two cDNA clones obtained from a human brain cDNA library (HFAP10 and HFAP20) and by a cDNA clone obtained from a mouse liver cDNA library (MFAP23; mouse PTP-BAS type 5b). Numbers indicate amino acid positions relative to human PTP-BAS type 1. C-termini are indicated by "COOH." VLFDK (SEQ ID NO: 21) indicates insertions in GLGF2 of HFAP10 (PTP-BAS type 4) and HFAP20 (PTP-BAS type 5a). The solid box at the C-terminus of HFAP20 and the stipled box at the C-terminus of MFAP23 indicate amino acid sequences that diverge from the other members of the PTP-BAS family of proteins. HFAP20 and MFAP23 terminate as shown and, therefore, do not contain a catalytic phosphatase domain.

Figure 8:
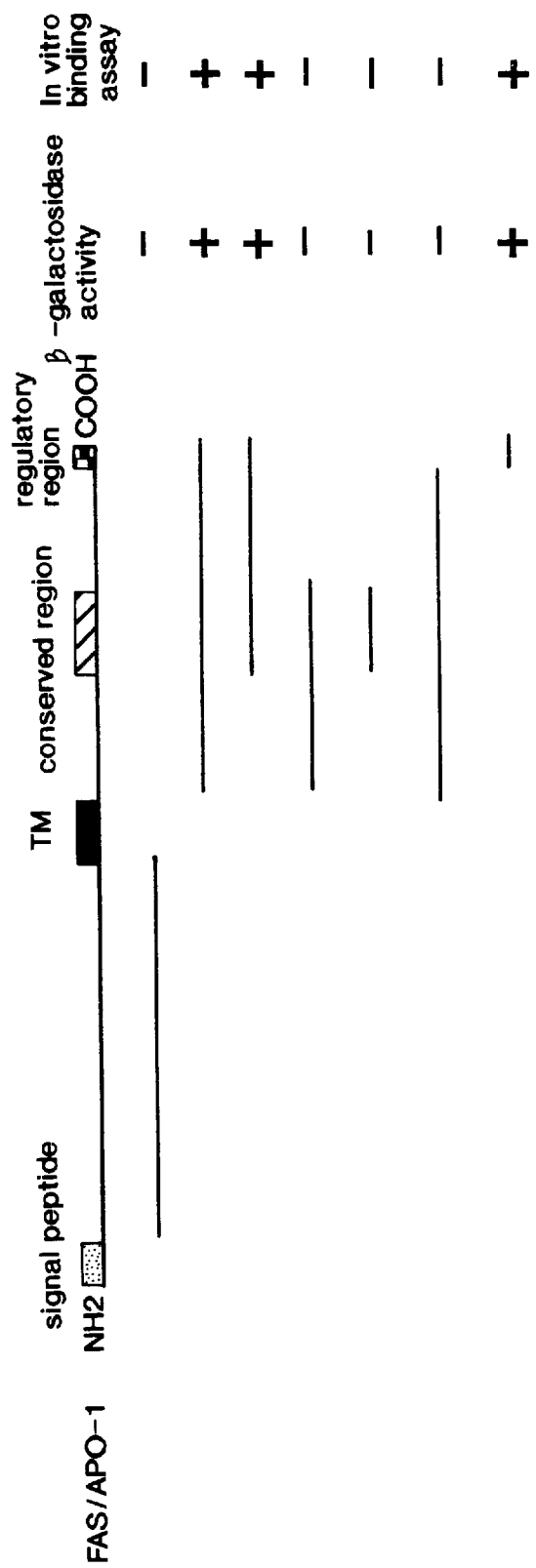

FIG. 8 demonstrates the ability of the polypeptide encoded by pVP16-31 to associate with various fragments of Fas. A schematic representation of the full length Fas protein is shown. Solid lines below the schematic of Fas indicate various fragments of Fas that were examined for binding to the polypeptide encoded by pVP16-31. The column labelled "β-galactosidase activity" indicates those fragments that bound (+) the pVP16-31 polypeptide and, as a result, produced a transcriptionally active complex in the two hybrid assay (see Example I) or did not bind (–). The column labelled "In vitro binding assay" indicates those fragments of Fas that bound (+) or did not bind (–) to a GST/HFAP10 polypeptide fusion protein.

Figure 9:
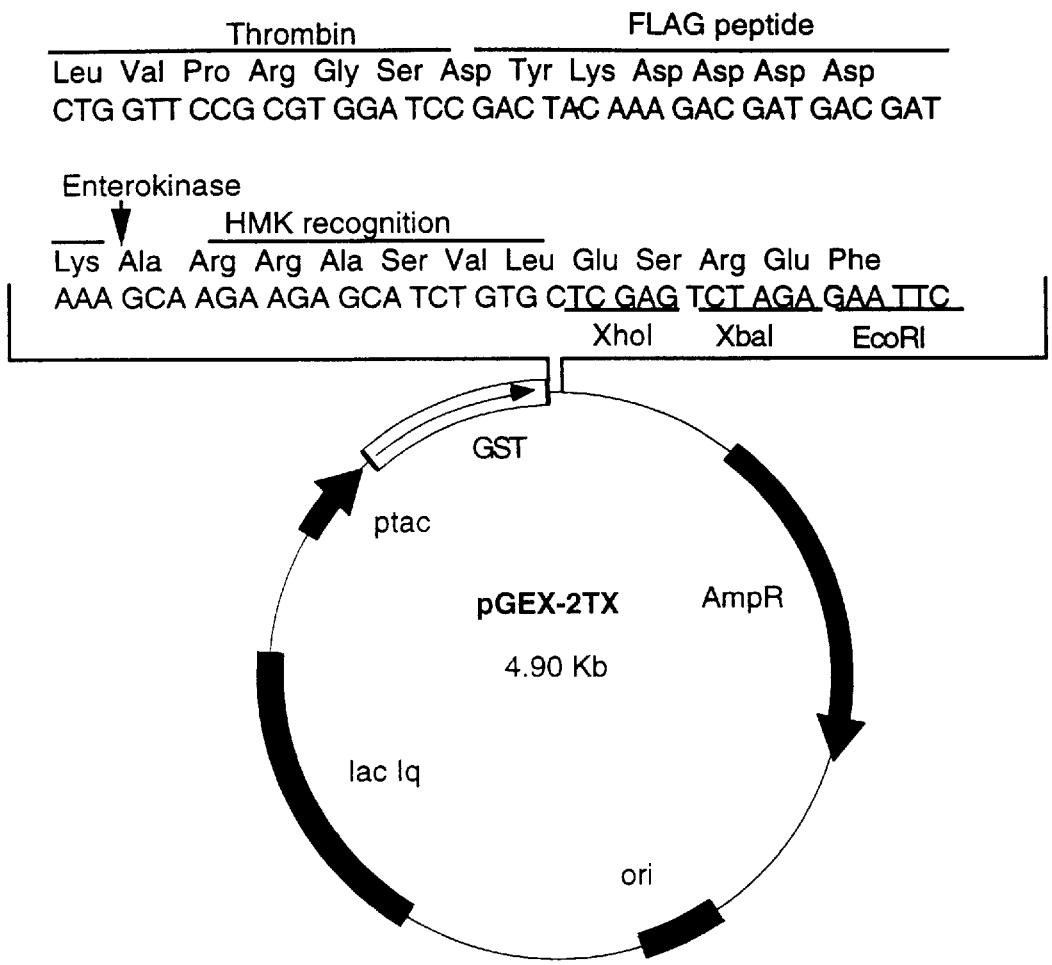

FIG. 9 provides a map of plasmid pGEX-2TX, which was used to produce GST/Fas fusion proteins. The plasmid contains a bacterial origin of replication (ori) and an ampicillin resistance gene (AmpR). Transcription of the sequence encoding the GST fusion protein is regulated from a tac promotor (ptac). LacIq indicates lac repressor. The vector also encodes a polypeptide sequence encoding thrombin and enterokinase cleavage sites, the FLAG™ peptide, a heart muscle kinase recognition site (HMK recognition) and various unique restriction endonuclease sites as indicated.

Figure 10:
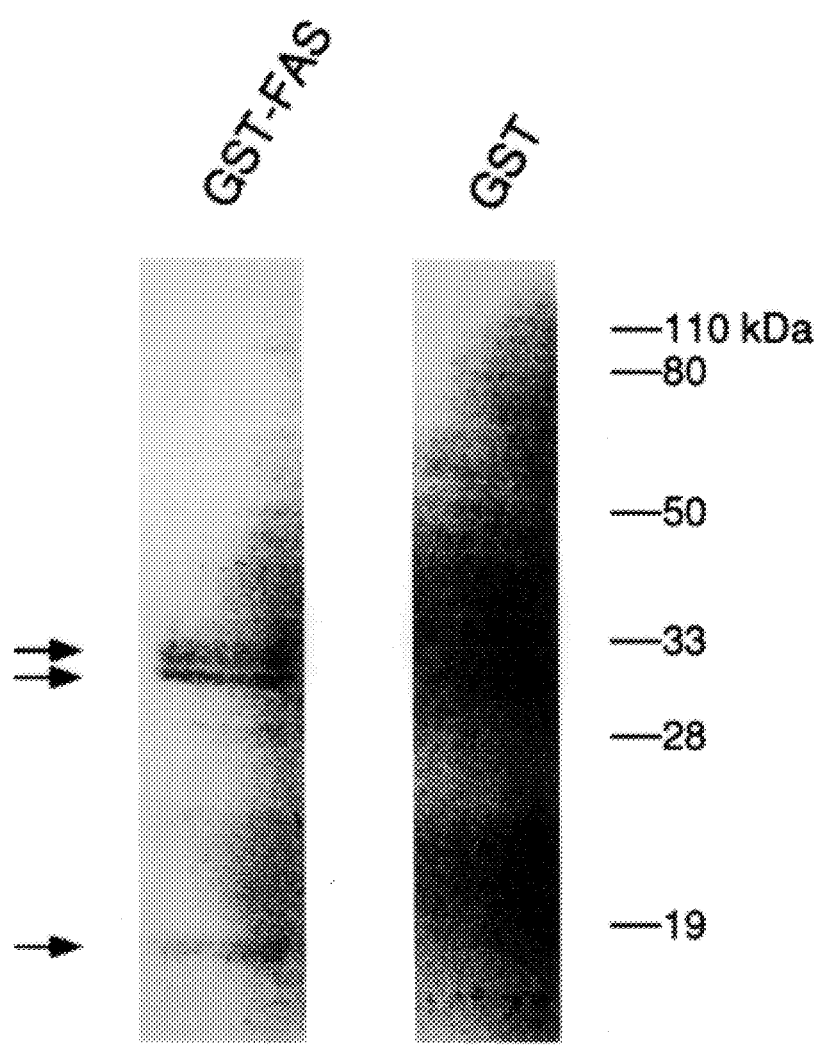

FIG. 10 is an autoradiograph of a far-western blot of mouse S49 T cell proteins probed with either a GST/Fas (119–335) (GST/FAS) fusion protein or GST, alone. Molecular weight markers are indicated at the right. Arrow indicate the migration of FAP's, which specifically bound GST/Fas(119–335).

Figure 11:
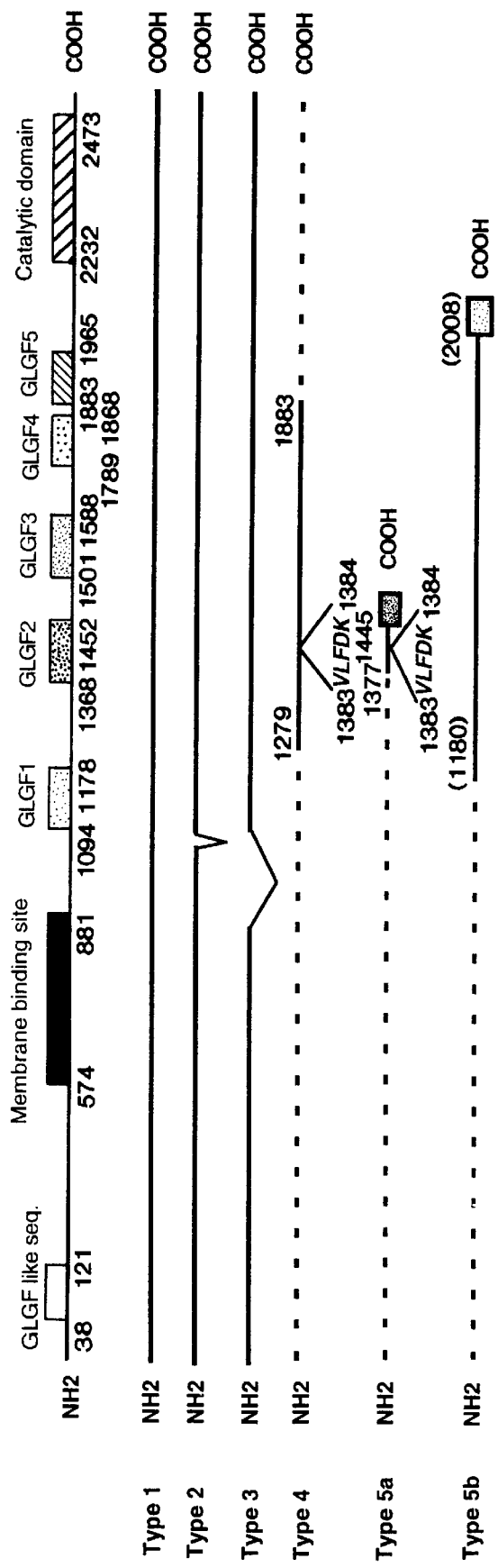

FIG. 11 schematically shows the amino acid sequences of six members of the PTP-BAS family of proteins, including the newly disclosed human PTP-BAS type 4 and two members of the subfamily of PTP-BAS type 5 proteins, human PTP-BAS type 5a and mouse PTP-BAS type 5b. Deleted segments in the alternatively spliced forms of PTP-BAS type 2 and type 3 are indicated (see Maekawa et al., FEBS Lett. 337:200–206 (1994), which is incorporated herein by reference). Numbers indicate the amino acid positions relative to human PTP-BAS type 1. The amino acid sequences of the various PTP-BAS isoforms are indicated by the solid line and correspond to the domains indicated at the top of the figure (GLGF (SEQ ID NO:20) is as in FIG. 6). Dashed lines indicate predicted amino sequences for human PTP-BAS type 4, human PTP-BAS type 5a and mouse PTP-BAS type 5b. VLFDK (SEQ ID NO:21) indicates the single letter amino acid code for the insertion in GLGF2 in human PTP-BAS type 4 and human PTP-BAS type 5a. The solid boxed region of human PTP-BAS type 5a and the stipled box in mouse PTP-BAS type 5b indicate the amino acid sequences that diverge from the other members of the PTP-BAS family.

FIG. 12 lists the deduced amino acid sequence (SEQ ID NO: 1) corresponding the cloned PTP-BAS type 4 (HFAP10). The single letter amino acid code is used. Numbers indicate the amino acid position relative to amino acid 1 in PTP-BAS type 1. Underlined amino acids indicate GLGF (SEQ ID NO:21) repeats. Bold print and italics indicate the VLFDK (SEQ ID NO:21) insertion in GLGF2.

FIG. 13 lists the nucleotide sequence (SEQ ID NO: 2) of the cloned PTP-BAS type 4 (HFAP10). Numbers indicate the nucleotide position relative to the transcription start site of the nucleic acid molecule encoding PTP-BAS type 1 and the corresponding amino acid position. Underlined nucleotides indicate sequences encoding GLGF (SEQ ID NO:20) repeats. Bold print and italics indicate the sequences encoding the VLFDK (SEQ ID NO:21) insertion in GLGF2.

FIG. 14 lists the deduced amino acid sequence (SEQ ID NO: 3) corresponding the cloned human PTP-BAS type 5a (HFAP20). The single letter amino acid code is used. Numbers indicate the amino acid position relative to amino acid 1 in PTP-BAS type 1. Underlined amino acids indicate a GLGF (SEQ ID NO:20) repeat. Bold and italics, together, indicate the VLFDK (SEQ ID NO:21) insertion in GLGF2. Italics, alone, indicate the amino acid sequence that diverges from other members of the PTP-BAS family. The * indicates the location of a STOP codon.

FIG. 15 lists the nucleotide sequence (SEQ ID NO: 4 and SEQ ID NO:22) of the cloned human PTP-BAS type 5a (HFAP20). Numbers indicate the nucleotide position relative to the transcription start site of the nucleic acid molecule encoding PTP-BAS type 1 and the corresponding amino acid position. Underlined nucleotides indicate sequences encoding GLGF (SEQ ID NO:20) repeats. Bold and italic, together, indicate the sequences encoding the VLFDK (SEQ ID NO:21) insertion in GLGF2. Italics, alone, indicate the sequence that diverges from other members of the PTP-BAS family. [—] indicates approximately 600 nucleotides that have not yet been sequenced. Underlining and italics, together, indicate STOP codon (TGA and TAA) and a polyadenylation signal (AATAAA).

FIG. 16 lists the deduced amino acid sequence (SEQ ID NO: 5) corresponding the cloned mouse PTP-BAS type 5b (MFAP23). The single letter amino acid code is used. Numbers indicate the amino acid position relative to amino acid 1 in human PTP-BAS type 1. Italics indicate the amino acid sequence that diverges from other members of the PTP-BAS family. The * indicates the location of a STOP codon.

FIG. 17 lists the nucleotide sequence (SEQ ID NO: 6) of the cloned mouse PTP-BAS type 5b (MFAP23). Numbers indicate the nucleotide position relative to the transcription start site of the nucleic acid molecule encoding human PTP-BAS type 1. Italics indicate the sequence that diverges from other members of the PTP-BAS family (beginning at position 6022). Underlining indicates STOP codons (TAA and TAG).

Figure 18:
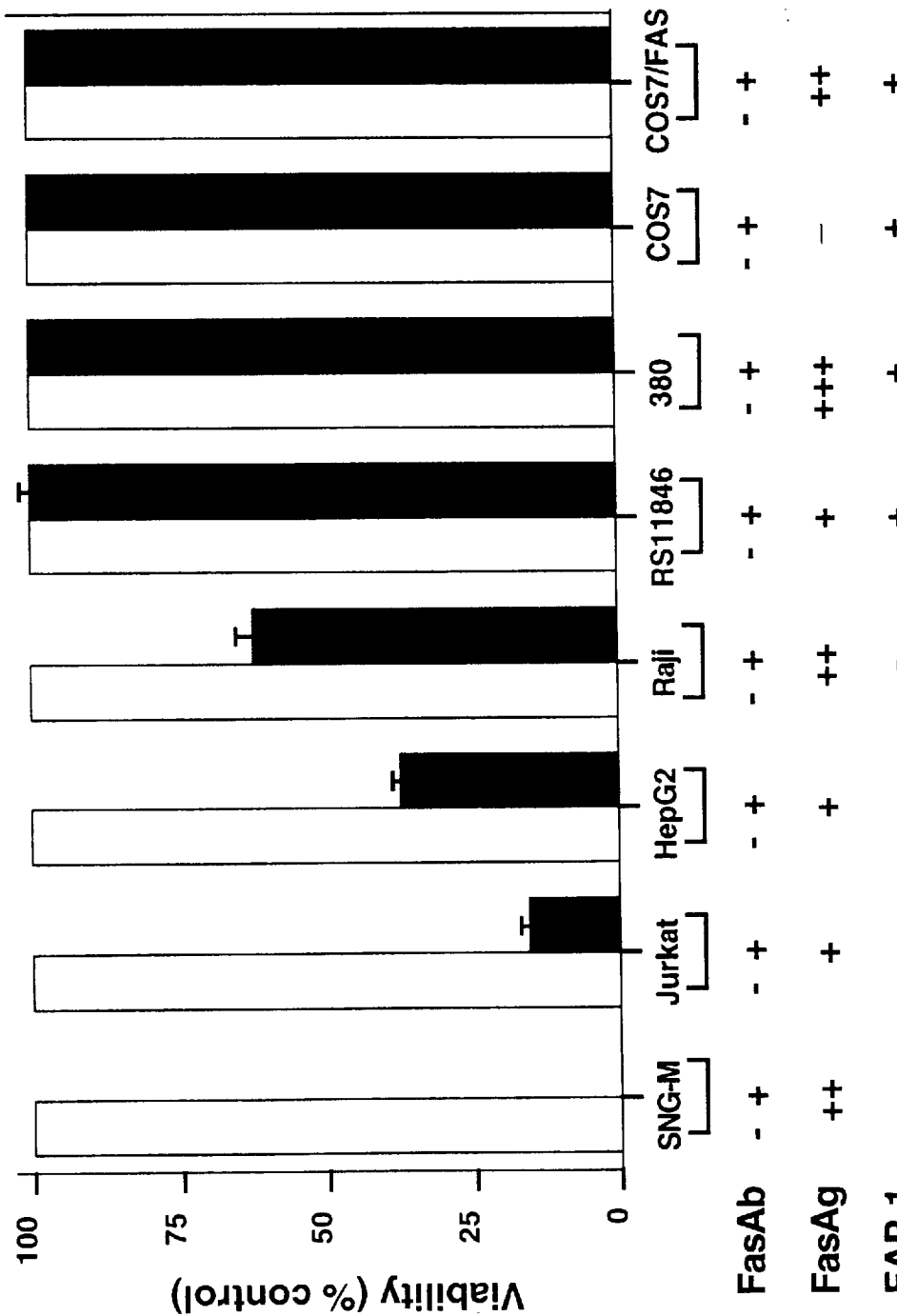

FIG. 18 shows the effect of PTP-BAS type 4 expression on apoptosis induced by anti-Fas antibody. The viability of various tumor cell lines as indicated was determined by trypan blue exclusion. Open bars show control viability (normalized to 100%) as determined in the absence of anti-Fas antibody (FasAb; "–"). Viability of cell exposed to anti-Fas antibody ("+") is shown by the solid bars. Relative amounts of Fas (FasAg) and PTP-BAS type 4 (PTP-BAS 4) expressed by the tumor cells is indicated ("–" means no expression detected).

Figure 19:
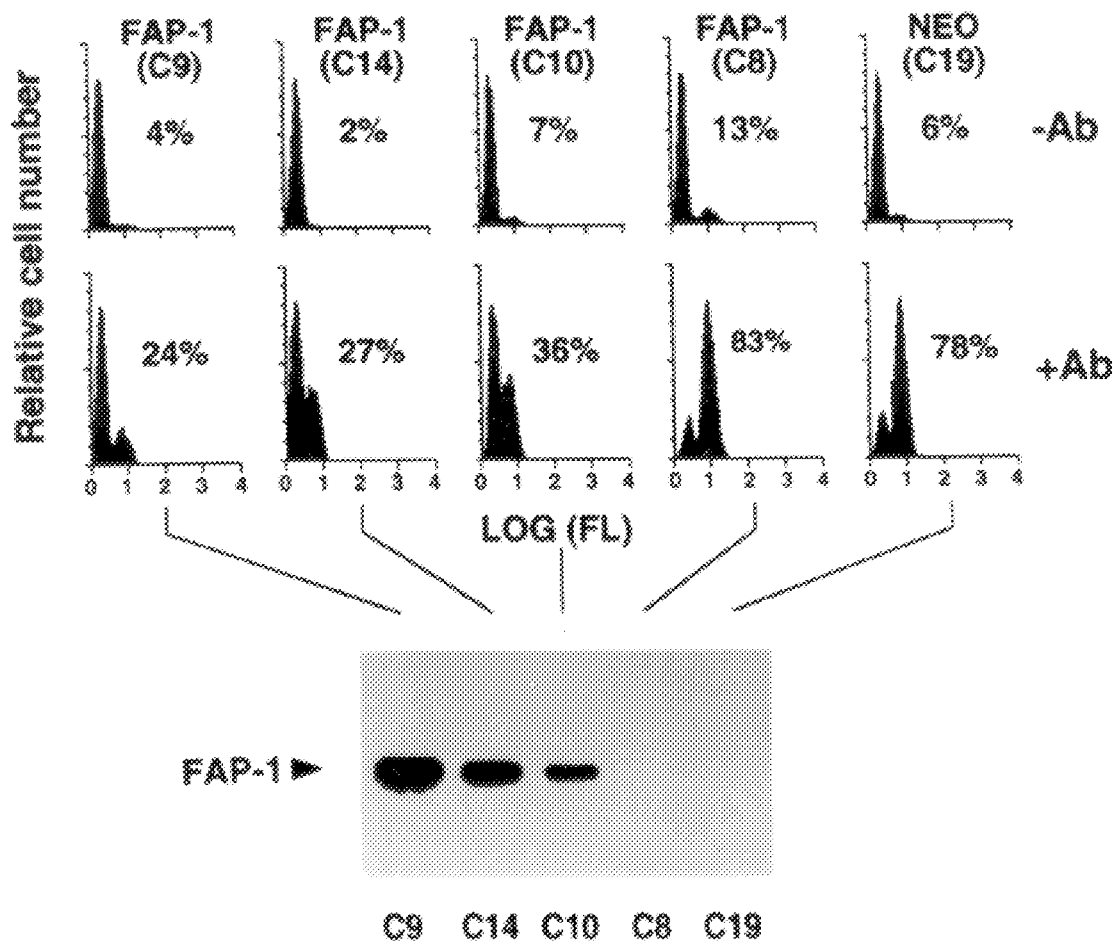

FIG. 19 demonstrates that Jurkat cells stably transfected to express human PTP-BAS type 4 are relatively resistant to anti-Fas antibody-induced apoptosis and that the amount of resistance is correlated to the amount of PTP-BAS type 4 expressed in the cells. The relative amount of PTP-BAS type 4 ("FAP-1") expressed in various stably transfected clones (C9, C14, C10 and C8) was determined by northern blot analysis (autoradiograph shown). Clone C19 was transfected with a control plasmid ("NEO"). Cells were treated with anti-Fas antibody for 4 hr, then cells with fragmented DNA due to apoptosis were detected by end labelling of 3'OH-DNA using biotinylated dUTP and terminal deoxynucleotide transferase (TdT) followed by FITC-avidin and examined by flow cytometry. Results are expressed as relative cell number (y-axis) and the log of the fluorescence intensity ("LOG (FL)"; x-axis). Untreated cells (–Ab) and anti-Fas antibody treated cells (+Ab) are shown. Percentages indicate the percent dead cells.

DETAILED DESCRIPTION OF THE INVENTION

The present invention provides novel Fas-associated proteins (FAP's), designated PTP-BAS type 4 and PTP-BAS type 5, which are alternatively spliced forms of a protein tyrosine phosphatase (PTPase) that was originally isolated from basophils (PTP-BAS). Unlike previously described isoforms of PTP-BAS, PTP-BAS types 4 and 5 each contain a 5 amino acid insertion in a sequence that is otherwise conserved among the members of the PTP-BAS family of proteins. In addition, the invention provides a subfamily of PTP-BAS type 5 proteins such as human PTP-BAS type 5a and mouse PTP-BAS type 5b, which diverge from the other members of the PTP-BAS family of proteins at their C-termini. As a result of this sequence divergence, PTP-BAS type 5 proteins lack a catalytic phosphatase domain and, therefore, are non-catalytic forms of PTP-BAS (see FIGS. 7 and 11).

As used herein, the term "Fas-associated protein" or "FAP" means a protein that can specifically bind to Fas, which is a cell surface receptor involved in apoptosis. A FAP can be identified, for example, using the binding assays described in Examples I and II. Various FAP's are disclosed herein, including the members of the PTP-BAS family of proteins (FIG. 11) and the 78 kilodalton (kDa) glucose regulated protein (GRP78; described below). Additional FAP's can be identified using the methods disclosed herein.

Although the term "FAP" is used generally, it should be recognized that a FAP that is identified using an assay described herein can be a portion of a protein, which is considered to be a candidate FAP. As used herein, the term "candidate FAP" refers to a protein that corresponds to a polypeptide sequence that can bind Fas but that consists of only a portion of the full length protein. For example, a FAP such as a PTP-BAS type 4 or a PTP-BAS type 5 can be identified by obtaining cDNA sequences from a cDNA library, expressing the polypeptides encoded by the cDNA sequences and detecting polypeptides that can bind Fas. Although such polypeptides are considered FAP's, it is well known that a cDNA sequence obtained from a cDNA library may not encode the full length protein. Thus, a cDNA can encode a polypeptide such as a PTP-BAS type 4 or a PTP-BAS type 5 that is only a portion of a full length protein but, nevertheless, assumes an appropriate conformation so as to bind Fas. However, in the full length protein, the polypeptide can assume a conformation that does not bind Fas due, for example, to steric blocking of the Fas binding site. Such a full length protein is an example of a candidate FAP. For convenience of discussion, the term "FAP" as used herein is intended to include a candidate FAP. Thus, a FAP can be a protein or a polypeptide portion of a protein that can bind Fas.

Since Fas is involved in apoptosis, the association of a FAP with Fas can affect the level of apoptosis in a cell. Fas is a cell surface protein that can trigger apoptosis in a cell (Itoh et al., *Cell* 66:233–243 (1991), which is incorporated herein by reference). Fas is a 36 kDa polypeptide that contains 319 amino acids. The cysteine-rich extracellular domain of Fas is similar to the p55 and p75 forms of the tumor necrosis factor receptor (TNFR) as well as to other members of the TNFR family, including the nerve growth factor receptor and receptors designated OX40, CD30 and CD40 (Oehm et al., *J. Biol. Chem.* 267:10709–10715 (1992) ). These members of the TNFR family of receptors can transduce extracellular signals that impact cell survival. The cytoplasmic domain of Fas (amino acids 191 to 335) is highly homologous with a TNFR and is essential for Fas function. Thus, proteins that can bind to the cytoplasmic domain of Fas can be signal transducing molecules in a Fas-mediated cell death pathway. The present invention provides FAP's, which can associate with the cytoplasmic domain of Fas and, therefore, can be involved in regulating apoptosis.

Fas is expressed on various types of human cells, including solid tumors of the breast, colon, prostate and pancreas. The ligand for the Fas receptor has been cloned and is present on cytologic T lymphocytes (Suda et al., *Cell* 75:1169–1178 (1993)). The presence of the Fas ligand on T cells indicates that Fas can act as a target that allows effector cells of the immune system to recognize and attack a cancer cell. The identification herein of various FAP's has provided the necessary insight into signal transduction pathways controlled by Fas and has allowed for the development of assays that are useful for identifying agents that effectively alter the association of a FAP and Fas. Such agents can be useful, for example, for providing effective therapy for a cancer in a subject or for treating an autoimmune disease.

A FAP such as a PTP-BAS type 4 or a PTP-BAS type 5 can be identified by detecting the association of the FAP with Fas. Such an association can be identified using an in vivo assay such as a yeast two hybrid assay (see Example I) or an in vitro assay (see Example II). As used herein, the term "associate" or "association" means that a FAP and Fas can bind to each other relatively specifically and, therefore, can form a bound complex. In particular, the association of a FAP and Fas is sufficiently specific such that the bound complex can form in vivo in a cell or in vitro under suitable conditions (see Example II). Other methods for determining whether a protein can bind Fas and, therefore, is a FAP are known and include, for example, equilibrium dialysis.

In a normal cell, a steady state level of association of a FAP and Fas likely occurs. This steady state level of association of a FAP and Fas in a particular cell type can determine the normal level of apoptosis in that cell type. An increase or decrease in the steady state level of association of a FAP and Fas in a cell can result in an increased or decreased level of apoptosis in the cell, which can result in a pathology in a subject. The normal association of a FAP and Fas in a cell can be altered due, for example, to the expression in the cell of a variant FAP or a variant Fas, either of which can compete for binding with the FAP that normally binds to Fas in the cell and, therefore, can decrease the association of a FAP and Fas in a cell. The term "variant" is used generally herein to mean a FAP or a Fas that is different from the FAP or Fas, respectively, that normally is found in a particular cell type. In addition, the normal association of a FAP and Fas in a cell can be increased or decreased due, for example, to contact of the cell with an agent such as a drug that can effectively alter the association of a FAP and Fas in a cell.

Several FAP's, including the newly described PTP-BAS types 4 and 5 (see below), were identified using the yeast two hybrid system (Fields and Song, *Nature* 340:245–246 (1989); Vojtek et al., *Cell* 74:205–214 (1993), each of which is incorporated herein by reference). An in vivo transcription activation assay such as the yeast two hybrid system is particularly useful for identifying and manipulating the association of proteins. In addition, the results observed in such an assay likely mirror the events that naturally occur in a cell. Thus, the results obtained in such an in vivo assay can be predictive of results that can occur in a cell in a subject such as a human subject.

A transcription activation assay such as the yeast two hybrid system is based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two proteins. The DNA-binding domain and trans-activation domain can be bridged, for example, by expressing the DNA-binding domain and trans-activation domain as fusion proteins (hybrids), provided that the proteins that are fused to the domains can associate with each other. The non-covalent bridging of the two hybrids brings the DNA-binding and trans-activation domains together and creates a transcriptionally competent complex. The association of the proteins is determined by observing transcriptional activation of a reporter gene (see Example I).

The yeast two hybrid systems exemplified herein use various strains of *S. cerevisiae* as host cells for vectors that express the hybrid proteins. A transcription activation assay also can be performed using, for example, mammalian cells. However, the yeast two hybrid system is particularly useful due to the ease of working with yeast and the speed with which the assay can be performed. For example, yeast host cells containing a lacZ reporter gene linked to a LexA operator sequence were used to demonstrate that a PTP-BAS can interact with Fas (Example I). The DNA-binding domain consisted of the LexA DNA-binding domain, which binds the LexA promoter, fused to a portion of Fas and the trans-activation domain consisted of either the B42 acidic region or the VP16 trans-activation domain fused to cDNA sequences, some of which encoded FAP's. When the LexA domain was non-covalently bridged to a trans-activation domain fused to a FAP, the association of Fas and the FAP activated transcription of the reporter gene.

A FAP also can be identified using an in vitro assay such as an assay utilizing, for example, a glutathione-S-transferase (GST) fusion protein as described in Example II. Such an in vitro assay provides a simple, rapid and inexpensive method for identifying and isolating a FAP. Such an in vitro assay is particularly useful in confirming results obtained in vivo and can be used to characterize specific binding domains of a FAP (see Example II). For example, a GST/Fas fusion protein can be expressed and can be purified by binding to an affinity matrix containing immobilized glutathione. If desired, a sample that can contain a FAP or active fragments of a FAP can be passed over an affinity column containing bound GST/Fas and a FAP that binds to Fas can be obtained. In addition, GST/Fas can be used to screen a cDNA expression library, wherein binding of the Fas fusion protein to a clone indicates that the clone contains a cDNA encoding a FAP.

Using these in vitro and in vivo assays, various FAP's have been identified, including the newly described human PTP-BAS type 4, human PTP-BAS type 5a and mouse PTP-BAS type 5b. PTP-BAS is a PTPase that originally was cloned from human basophils (Maekawa et al. *FEBS Lett.* 337:200–206, 1994, which is incorporated herein by reference). Three isoforms of PTP-BAS, which are formed due to naturally-occurring in-frame deletions that result because of alternative splicing, were known prior to the present disclosure. PTP-BAS originally was identified by the reverse transcriptase-polymerase chain reaction cloning method using primers that were directed to sequences that are conserved among PTPase's. The function of PTP-BAS was not known prior to the present disclosure, which demonstrates that PTP-BAS can associate with the cytoplasmic domain of Fas and, in particular, with a C-terminal region of Fas, and that the level of expression of a PTP-BAS in a cell correlates with resistance of the cell to Fas-induced apoptosis (see Example V).

The previously described isoforms of PTP-BAS are designated type 1 (2,485 amino acids), type 2 (2,466 amino acids) and type 3 (2,294 amino acids) and, as disclosed herein, are FAP's. PTP-BAS types 2 and 3 are alternatively spliced forms of PTP-BAS type 1 and contain deletions of 19 and 191 amino acids, respectively (see FIG. 11). These deletions are located immediately upstream of three glycine-leucine-glycine-phenylalanine (GLGF SEQ ID NO:20) repeats, which are homologous to a sequence found in guanylate kinases (FIG. 11).

PTP-BAS types 1, 2 and 3 each contain a single PTPase catalytic domain at their carboxy termini (see FIG. 11). These three PTP-BAS isoforms each also have an amino terminal membrane-binding domain that is similar in sequence to a domain present in several cytoskeleton-associated proteins. In addition, as disclosed herein, PTP-BAS types 1, 2 and 3 can bind Fas (see Example I).

The present invention provides substantially purified mammalian PTP-BAS type 4 and PTP-BAS type 5 proteins, which are alternatively spliced forms of PTP-BAS. Since the PTP-BAS type 4 and type 5 proteins can bind Fas, they are FAP's. In contrast to the previously known human PTP-BAS types 1, 2 and 3, human PTP-BAS type 4 and type 5a contain a 5 amino acid insertion in the otherwise conserved GLGF2 repeat (see FIG. 11). In addition, the C-termini of the members of the subfamily of PTP-BAS type 5 proteins diverge in sequence from the other members of the PTP-BAS family of proteins and, as a result, PTP-BAS type 5 proteins such as human PTP-BAS type 5a and mouse PTP-BAS type 5b do not contain a catalytic phosphatase domain (see FIGS. 7 and 11).

The invention provides substantially purified mammalian PTP-BAS type 4 comprising substantially the amino acid sequence of human PTP-BAS type 4 shown in FIG. 12 (SEQ ID NO: 1), which was derived from the nucleotide sequence shown in FIG. 13 (SEQ ID NO: 2). In addition, the invention provides a subfamily of substantially purified mammalian PTP-BAS type 5 proteins comprising, for example, substantially the amino acid sequence of human PTP-BAS type 5a shown in FIG. 14 (SEQ ID NO: 3), which was derived from the nucleotide sequence shown in FIG. 15 (SEQ ID NO: 4 and SEQ ID NO:22), or substantially the amino acid sequence of mouse PTP-BAS type 5b shown in FIG. 16 (SEQ ID NO: 5), which was derived from the nucleotide sequence shown in FIG. 17 (SEQ ID NO: 6). PTP-BAS type 4 and type 5 proteins have been characterized as members of the PTP-BAS family of proteins based on their homology with other members of this protein family (see FIGS. 7 and 11; see, also, Examples III and IV).

As used herein, the term "substantially the amino acid sequence" means the disclosed amino acid sequence for human PTP-BAS type 4 (SEQ ID NO: 1), a human PTP-BAS type 5a (SEQ ID NO: 3) or a mouse PTP-BAS type 5b (SEQ ID NO: 5), as well as amino acid sequences that are similar to SEQ ID NO: 1, SEQ ID NO: 3 or SEQ ID NO: 5, respectively, but have one or more amino acid additions, deletions or substitutions that do not substantially alter the ability of the encoded protein to function like a PTP-BAS type 4 or a PTP-BAS type 5 and, for example, bind Fas. As used herein, the term "substantially purified" means a protein that is in a form that is relatively free from contaminating lipids, proteins, nucleic acids or other cellular material normally associated with a protein in a cell. A substantially purified human PTP-BAS type 4, human PTP-BAS type 5a or mouse PTP-BAS type 5b protein can be obtained, for example, using well known biochemical methods of purification or by expressing a recombinant nucleic acid molecule encoding a PTP-BAS such as the nucleic acid molecules shown as SEQ ID NO: 2, SEQ ID NO: 4, (SEQ ID NO:22) or SEQ ID NO: 6, respectively. In addition, an amino acid sequence consisting of at least a portion of the amino acid sequences of SEQ ID NO: 1, SEQ ID NO: 3 or SEQ ID NO: 5 can be chemically synthesized or can be produced by expressing a portion of the nucleotide sequences shown as SEQ ID NO: 2, SEQ ID NO: 4, SEQ ID NO:22 or SEQ ID NO: 6, respectively.

As used herein, the terms "protein" or "polypeptide" are used in the broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of a FAP as defined below can be an example of such a polypeptide. A protein can be a complete, full length gene product, which can be a core protein having no amino acid modifications or can be a post-translationally modified form of a protein such as a phosphoprotein, glycoprotein, proteoglycan, lipoprotein and nucleoprotein.

In reference to a FAP such as a PTP-BAS type 4 or a PTP-BAS type 5, a protein is characterized primarily by its ability to associate with Fas. As used herein, the term "Fas" means the full length Fas protein or a portion of the full length Fas protein such as the Fas(191–335) or Fas (321–335) portions of Fas, either of which can associate with a FAP (see Example II and FIG. 6). It also should be recognized that the ability of a FAP to associate with Fas can be due to a portion of the full length FAP as is disclosed herein for PTP-BAS type 4 and for the members of the subfamily of PTP-BAS type 5 proteins. Thus, a FAP can be an active fragment of a full length protein. As used herein, the term "active fragment" means a FAP that is a portion of a full length protein, provided that the portion has an activity that is characteristic of the corresponding full length protein. For example, an active fragment of a FAP such as a PTP-BAS type 4 or a PTP-BAS type 5 polypeptide as disclosed herein or a GLGF2 domain of PTP-BAS can have an activity such as the ability to bind Fas or can have an activity as an immunogen, which can be used to obtain an anti-FAP antibody. Thus, the invention also provides active fragments of a PTP-BAS type 4 or a member of the subfamily of PTP-BAS type 5 proteins, which can be identified using the assays described below. As used herein, the term "subfamily of PTP-BAS type 5 proteins" means PTP-BAS proteins that do not contain a catalytic phosphatase domain (see, for example, FIG. 7). As disclosed herein, human PTP-BAS type 5a and mouse PTP-BAS type 5b are examples of members of the subfamily of PTP-BAS type 5 proteins. The term "PTP-BAS type 5" is used generally herein to refer to the members of the subfamily of PTP-BAS type 5 proteins.

The present invention also provides an anti-PTP-BAS type 4 antibody and an anti-PTP-BAS type 5 antibody, including, for example, an anti-human PTP-BAS type 5a antibody or an anti-mouse PTP-BAS type 5b antibody. It should be recognized that an antibody of the invention can be specific for an epitope that is present only in a particular type of PTP-BAS or can be specific for an epitope that is common to more than one type of PTP-BAS. For example, an anti-PTP-BAS type 5 antibody can be specific for a single member of the subfamily of PTP-BAS type 5 proteins such as the human PTP-BAS type 5a protein or can be specific for more than one member of this subfamily. As used herein, the term "antibody" is used in its broadest sense to include polyclonal and monoclonal antibodies, as well as polypeptide fragments of antibodies that retain a specific binding activity for a specific antigen of at least about $1 \times 10^5 M^{-1}$. One skilled in the art would know that anti-PTP-BAS type 4 antibody fragments or anti-PTP-BAS type 5 antibody fragments such as Fab, F(ab')$_2$, Fv and Fd fragments can retain specific binding activity for a PTP-BAS type 4 or a PTP-BAS type 5, respectively, and, thus, are included within the definition of an antibody. In addition, the term "antibody" as used herein includes naturally occurring antibodies as well as non-naturally occurring antibodies and fragments of antibodies that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

An anti-PTP-BAS type 4 antibody or an anti-PTP-BAS type 5 antibody can be prepared using well known methods as described, for example, by Harlow and Lane, *Antibodies: A laboratory manual* (Cold Spring Harbor Laboratory Press, 1988), which is incorporated herein by reference. A PTP-BAS type 4 or a PTP-BAS type 5 protein or a portion of a PTP-BAS type 4 or a PTP-BAS type 5 protein can be used as an immunogen. Such an immunogen can be prepared from natural sources or produced recombinantly or, in the case of a portion of the protein, can be chemically synthesized. Non-immunogenic peptides of a PTP-BAS type 4 or a PTP-BAS type 5 protein can be made immunogenic by coupling the hapten to a carrier molecule such bovine serum albumin (BSA) or keyhole limpet hemocyanin (KLH) as described, for example, by Harlow and Lane, supra, 1988). In addition, a PTP-BAS type 4 or a PTP-BAS type 5 fusion protein can be expressed as described in Example II. Such a fusion protein can be readily purified and used as an immunogen. Using these methods, various anti-FAP antibodies have been obtained (not shown).

Polyclonal antibodies can be raised, for example, in rabbits. In addition, monoclonal antibodies can be obtained using well known methods (see, for example, Reed et al., *Anal. Biochem.* 205:70–76 (1992)), which is incorporated herein by reference; see, also, Harlow and Lane, supra, (1988)). For example, spleen cells from an immunized mouse can be fused to an appropriate myeloma cell line such as SP/02 myeloma cells to produce hybridoma cells. Cloned hybridoma cell lines can be screened using a labelled immunogen such as PTP-BAS type 4 or type 5 to identify clones that secrete monoclonal antibodies. Hybridomas that express antibodies having a desirable specificity and affinity can be isolated and utilized as a continuous source of antibodies. One skilled in the art would know that a dependable source of monoclonal antibodies is desirable, for example, for preparing diagnostic kits as described below.

The invention also provides a substantially purified nucleic acid molecule, which encodes a mammalian PTP-BAS type 4, comprising substantially the nucleotide sequence encoding human PTP-BAS type 4 as shown in FIG. 13 (SEQ ID NO: 2). In addition, the invention provides a substantially purified nucleic acid molecule, which encodes a mammalian PTP-BAS type 5, comprising, for example, substantially the nucleotide sequence encoding human PTP-BAS type 5a as shown in FIG. 15 (SEQ ID NO: 4 and SEQ ID NO:22) or substantially the nucleotide sequence encoding mouse PTP-BAS type 5b as shown in FIG. 17 (SEQ ID NO: 6).

As used herein, the term "substantially purified" means a nucleic acid molecule that is in a form that is relatively free from contaminating lipids, proteins, nucleic acids or other cellular material normally associated with a nucleic acid molecule in a cell. A substantially purified nucleic acid molecule can be obtained, for example, by recombinant DNA methods as described herein (see, also, Sambrook et al., *Molecular Cloning: A laboratory manual* (Cold Spring Harbor Laboratory Press 1989), which is incorporated herein by reference) or can be chemically synthesized. As used herein, the term "substantially the nucleotide sequence" means the disclosed nucleotide sequence for human PTP-BAS type 4 (SEQ ID NO: 2), human PTP-BAS type 5a (SEQ ID NO: 4 and SEQ ID NO:22) or mouse PTP-BAS type 5b (SEQ ID NO: 6), as well as a similar sequence that contains, for example, different nucleotides than shown in SEQ ID NO: 2, SEQ ID NO: 4, SEQ ID NO:22 or SEQ ID NO: 6, but that, as a result of the degeneracy of the genetic code, encodes substantially the same amino acid sequence as shown in SEQ ID NO: 1, SEQ ID NO: 3 or SEQ ID NO: 5, respectively. In addition, a nucleic acid molecule of the invention also can encode a portion of a PTP-BAS type 4 or a PTP-BAS type 5 protein, including, for example, an active fragment of a PTP-BAS type 4 or a PTP-BAS type 5 protein.

The invention also provides a nucleotide sequence that can hybridize to a portion of a nucleic acid molecule encoding a PTP-BAS type 4 or a PTP-BAS type 5 or both PTP-BAS types 4 and 5 under relatively stringent hybridization conditions. Such a nucleotide sequence should be at least ten nucleotides in length and can be prepared, for example, by restriction endonuclease digestion of a cloned nucleic acid molecule encoding a PTP-BAS type 4 or a PTP-BAS type 5, by PCR amplification of a portion of the nucleic acid molecule shown in FIG. 13 (SEQ ID NO: 2), FIG. 15 (SEQ ID NO: 4 and SEQ ID NO:22) or FIG. 17

(SEQ ID NO: 6) or by chemical synthesis. Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. If desired, a hybridizing nucleotide sequence can be detectably labelled and used as a probe or can be used as a primer for PCR. Methods for detectably labelling a nucleotide sequence are well known in the art (see, for example, Sambrook et al., supra, 1989; see, also, Ausubel et al., *Current Protocols in Molecular Biology* (Greene Publ., N.Y. 1989), which is incorporated herein by reference).

For convenience, the term "PTP-BAS" is used generally herein to mean any or all isoforms of PTP-BAS, including, for example, the previously known PTP-BAS types 1, 2 and 3 and the newly disclosed PTP-BAS types 4 and 5. In addition, a PTP-BAS can be a mutant form of a PTP-BAS, which is a PTP-BAS that contains one or a few amino acid additions, deletions or substitutions, provided that the mutant PTP-BAS can bind Fas. For example, a mutant PTP-BAS can have a single amino acid substitution, which can result in the loss of PTPase activity without significantly affecting the ability of the mutant PTP-BAS to bind Fas. A mutant PTP-BAS can be obtained, for example, by site directed mutagenesis of a nucleic acid molecule encoding a PTP-BAS and screening the mutagenized nucleic acid molecules to identify a nucleic acid molecule that expresses a mutant PTP-BAS, which can bind Fas but lacks PTPase activity. Expression in a cell of a PTP-BAS that can bind Fas but that lacks catalytic activity, including, for example, a member of the subfamily of PTP-BAS type 5 proteins, a mutant PTP-BAS or a portion of a PTP-BAS such as the portion of PTP-BAS type 4 disclosed herein, can alter the association of a catalytic PTP-BAS to Fas and, therefore, can modulate the level apoptosis in a cell. As used herein, the term "modulate" means increase or decrease.

The present invention also provides another example of a FAP, the 78,000 dalton glucose-regulated protein (GRP78). GRP78 is a stress-related protein that is located in the endoplasmic reticulum of a cell and shares sequence homology with the major heat shock protein (Ting and Lee, *DNA* 7:275–278 (1988); Sugawara et al., *Canc. Res.* 53:6001–6005 (1993), each of which is incorporated herein by reference). Expression of GRP78 in a cell can decrease the susceptibility of the cell to T cell mediated cytotoxicity. As disclosed herein, GRP78 can associate with Fas and, therefore, is a FAP. Thus, GRP78 likely can modulate apoptosis in a cell based on its degree of association with Fas.

The identification of a FAP that can bind Fas, which is involved in apoptosis, provides a means to identify agents that can effectively alter the of associated of a FAP with a Fas. Thus, the present invention provides a screening assay useful for identifying an effective agent, which can alter the association of a FAP with Fas. Since Fas is involved in apoptosis, the identification of such effective agents can be useful for modulating the level of apoptosis in a cell in a subject having a pathology characterized by an increased or decreased level of apoptosis.

As used herein, the term "agent" means a chemical or biological molecule such as a simple or complex organic molecule, a peptide, a peptido-mimetic, a protein or an oligonucleotide that has the potential for altering the association of a FAP and Fas or altering the activity of a FAP. In addition, the term "effective agent" is used herein to mean an agent that can, in fact, alter the association of a FAP and Fas or can, in fact, alter the activity of a FAP.

As used herein, the term "alter the association" means that the association of a FAP and Fas either is increased or is decreased due to the presence of an effective agent. As a result of an altered association of a FAP and Fas in a cell, the activity of Fas or of the FAP can be increased or decreased, thereby modulating the level of apoptosis in the cell. As used herein, the term "alter the activity" means that the agent can increase or decrease the activity of a FAP in a cell, thereby modulating the level of apoptosis in the cell. For example, an effective agent can increase or decrease the phosphatase activity of a PTP-BAS, without affecting the association of the PTP-BAS with Fas. As disclosed herein, the expression of a PTP-BAS in a cell can increase the resistance of the cell to Fas-induced apoptosis, provided the expressed PTP-BAS contains the catalytic phosphatase domain (see Example V).

An effective agent can act by interfering with the ability of a FAP and a Fas to associate or can act by causing the dissociation of a bound FAP-Fas complex, wherein the ratio of bound FAP-Fas complex to free FAP and Fas is related to the level of apoptosis in a cell. For example, binding of a ligand to Fas can allow Fas, in turn, to bind a FAP such as a catalytic form of a PTP-BAS. The association, for example, of Fas and a catalytic PTP-BAS can result in activation or inhibition of the phosphatase activity of PTP-BAS. In the presence of an effective agent, the association of the catalytic PTP-BAS and Fas can be altered, which can alter the phosphatase activity of PTP-BAS in the cell. As a result of the altered phosphatase activity, the level of apoptosis in a cell can be increased or decreased. Thus, the identification of an effective agent that alters the association of Fas and a FAP can allow for the use of the effective agent to increase or decrease the level of apoptosis in a cell.

An effective agent can be useful, for example, to increase the level of apoptosis in a cell such as a cancer cell, which is characterized by having a decreased level of apoptosis as compared to its normal cell counterpart. An effective agent also can be useful, for example, to decrease the level of apoptosis in a cell such as a T lymphocyte in a subject having a viral disease such as acquired immunodeficiency syndrome, which is characterized by an increased level of apoptosis in an infected T cell as compared to a normal T cell. Thus, an effective agent can be useful as a medicament for altering the level of apoptosis in a subject having a pathology characterized by increased or decreased apoptosis. In addition, an effective agent can be used, for example, to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

A PTP-BAS that lacks catalytic activity but retains the ability to associate with Fas is an example of an effective agent, since the expression of a non-catalytic PTP-BAS in a cell can alter the association of a catalytic PTP-BAS and Fas. Thus, it should be recognized that a FAP can be an effective agent, depending, for example, on the normal FAP-Fas association that occurs in a particular cell type. In addition, an active fragment of a PTP-BAS or of GRP78 can be an effective agent, provided the active fragment can alter the association of a FAP and Fas in a cell. Such active fragments, which can be peptides as small as about five amino acids, can be identified, for example, by screening a peptide library (see, for example, Ladner et al., U.S. Pat. No: 5,223,409, which is incorporated herein by reference) to identify peptides that can bind Fas.

Similarly, a peptide or polypeptide portion of Fas also can be an effective agent. For example, the C-terminal fifteen amino acids of Fas can associate with a FAP (see Example II; FIG. 8). A peptide such as the C-terminal peptide of Fas can be useful, for example, for decreasing the association of a FAP and Fas in a cell by competing for binding to the FAP. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

A screening assay to identify an effective agent can be performed in vivo using the two hybrid system or can be performed in vitro as disclosed herein. The yeast two hybrid system, for example, can be used to screen a panel of agents to identify effective agents that alter the association of Fas and a FAP. An effective agent can be identified by detecting an altered level of transcription of a reporter gene. For example, the level of transcription of a reporter gene due to the bridging of a DNA-binding domain and trans-activation domain by Fas and FAP hybrids can be determined in the absence and in the presence of an agent. An effective agent, which alters the association between Fas and a FAP, can be identified by a proportionately altered level of transcription of the reporter gene as compared to the control level of transcription in the absence of the agent.

In some cases, an agent may not be able to cross the yeast cell wall and, therefore, cannot enter a yeast cell to alter the association of a FAP and Fas. The use of yeast spheroplasts, which are yeast cells that lack a cell wall, can circumvent this problem (Smith and Corcoran, In *Current Protocols in Molecular Biology* (ed. Ausubel et al.; Greene Publ., N.Y. 1989), which is incorporated herein by reference). In addition, an agent, upon entering a cell, may require "activation" by a cellular mechanism, which may not be present in yeast. Activation of an agent can include, for example, metabolic processing of the agent or a modification such as phosphorylation of the agent, which can be necessary to convert the agent into an effective agent. In this case, a mammalian cell line can be used to screen a panel of agents. A transcription assay such as the yeast two hybrid system described in Example I can be adapted for use in mammalian cells using well known methods (see, for example, Fearon et al., *Proc. Natl. Acad. Sci., USA* 89:7958–7962 (1992), which is incorporated herein by reference; see, also, Sambrook et al., supra, 1989; Ausubel et al., supra, 1989).

The present invention also provides in vitro screening assays. Such screening assays are particularly useful in that they can be automated, which allows for high through-put screening, for example, of randomly or rationally designed agents such as drugs, peptido-mimetics or peptides in order to identify those agents that effectively alter the association of a FAP and Fas or the activity of a FAP and, thereby, modulate apoptosis. An in vitro screening assay can utilize, for example, a FAP or a FAP fusion protein such as a FAP-glutathione-S-transferase fusion protein (GST/FAP; see Example II). For use in the in vitro screening assay, the FAP or FAP fusion protein should have an affinity for a solid substrate as well as the ability to associate with Fas. For example, when a FAP is used in the assay, the solid substrate can contain a covalently attached anti-FAP antibody. Alternatively, a GST/FAP fusion protein can be used in the assay and the solid substrate can contain covalently attached glutathione, which is bound by the GST component of the GST/FAP fusion protein. Similarly, Fas or a GST/Fas fusion protein can be used in an in vitro assay as described herein.

An in vitro screening assay can be performed by allowing a FAP or FAP-fusion protein, for example, to bind to the solid support, then adding Fas and an agent to be tested. Control reactions, which do not contain an agent, can be performed in parallel. Following incubation under suitable conditions, which include, for example, an appropriate buffer concentration and pH and time and temperature that permit binding of the particular FAP and Fas, the amount of a FAP and Fas that have associated in the absence of an agent and in the presence of an agent can be determined. The association of a FAP and Fas can be detected, for example, by attaching a detectable moiety such as a radionuclide or a fluorescent label to Fas and measuring the amount of label that is associated with the solid support, wherein the amount of label detected indicates the amount of association of Fas and a FAP. By comparing the amount of specific binding in the presence of an agent as compared to the control level of binding, an effective agent, which alters the association of a FAP and Fas, can be identified. Such an assay is particularly useful for screening a panel of agents such as a peptide library in order to detect an effective agent.

The invention further provides methods for modulating apoptosis in a cell by introducing into the cell a nucleic acid molecule encoding a FAP or Fas or an antisense nucleotide sequence, which is complementary to a region of a gene encoding a FAP or Fas and can hybridize to the gene or to an mRNA transcribed from the gene. The level of apoptosis in a cell can be modulated by increasing or decreasing the expression of a FAP or Fas in a cell, which can alter the normal steady-state association of a FAP and Fas, thereby increasing or decreasing the activity of the FAP or of Fas in the cell. For example, the expression of human PTP-BAS type 4 in cell can render the cell relatively resistant to Fas-induced apoptosis as compared to the normal level of apoptosis in the cell (see Example V and FIG. 19). Thus, a nucleic acid molecule or an antisense nucleotide sequence as described above can be useful as a medicament for treating a pathology characterized by an increased or decreased level of apoptosis in a cell as compared to its normal cell counterpart.

A nucleic acid sequence encoding a FAP such as a PTP-BAS or GRP78 or an active fragment of a FAP can be expressed in a cell using well known expression vectors and gene transfer methods Sambrook et al., supra, (1989). Viral vectors that are compatible with a targeted cell are particularly useful for introducing a nucleic acid encoding a FAP into a cell. For example, recombinant adenoviruses having general or tissue-specific promoters can be used to deliver a nucleic acid encoding a FAP into a variety of cell types in various tissues and can direct expression of the nucleic acid in the target cell. Recombinant adeno-associated viruses also are useful for introducing a nucleic acid encoding a FAP into a cell and have the added advantage that the recombinant virus can stably integrate into the chromatin of even quiescent non-proliferating cells such as neurons of the central and peripheral nervous systems (Lebkowski et al., *Mol. Cell. Biol.* 8:3988–3996 (1988), which is incorporated herein by reference).

Such viral vectors are particularly useful where it is desirable to introduce a nucleic acid encoding a FAP into a cell in a subject, for example, for gene therapy. Viruses are specialized infectious agents that can elude host defense mechanisms and can infect and propagate in specific cell types. In particular, the specificity of viral vectors for particular cell types can be utilized to target predetermined cell types. Thus, the selection of a viral vector will depend, in part, on the cell type to be targeted. For example, if a neurodegenerative disease is to be treated by increasing the level of a FAP in neuronal cells affected by the disease, then a viral vector that targets neuronal cells can be used. A vector derived from a herpes simplex virus is an example of a viral vector that targets neuronal cells (Battleman et al., *J. Neurosci.* 13:941–951 (1993), which is incorporated herein by reference). Similarly, if a disease or pathological condition of the hematopoietic system is to be treated, then a viral vector that is specific for a particular blood cell or its precursor cell can be used. A vector based on a human immunodeficiency virus is an example of such a viral vector (Carroll et al., *J. Cell. Biochem.* 17E:241 (1993), which is incorporated herein by reference). In addition, a viral vector or other vector can be constructed to express a nucleic acid encoding a FAP in a tissue specific manner by incorporating a tissue-specific promoter or enhancer into the vector (Dai et al., *Proc. Natl. Acad. Sci., USA* 89:10892–10895 (1992), which is incorporated herein by reference).

Retroviral vectors can be particularly useful for introducing a nucleic acid encoding a FAP into a cell in vivo. Retroviral vectors can be constructed either to function as infectious particles or to undergo only a single initial round of infection. In the former case, the genome of the virus is modified so that it maintains the necessary genes, regulatory sequences and packaging signals to synthesize new viral proteins and RNA. However, genes conferring oncogenic potential of these viruses is destroyed. After the viral proteins are synthesized, the host cell packages the RNA into new viral particles, which can undergo further rounds of infection. The viral genome also is engineered to encode and express the desired recombinant gene.

In the case of non-infectious viral vectors, the helper virus genome can be mutated to destroy the viral packaging signal required to encapsulate the RNA into viral particles. However, the helper virus retains structural genes required to package a co-introduced recombinant virus containing a gene of interest. Without a packaging signal, a viral particle will not contain a genome and, thus, cannot proceed through subsequent rounds of infection. Methods for constructing and using viral vectors are known in the art and reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, a vector containing a nucleic acid encoding a FAP or Fas or an antisense nucleotide sequence can be administered to a subject by various methods. For example, if viral vectors are used, administration can take advantage of the target specificity of the vectors. In such cases, there in no need to administer the vector locally at the diseased site. However, local administration can be a particularly effective method of administering a nucleic acid encoding a FAP. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule encoding a FAP into cells in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., *Science* 259:1745–1748 (1993), which is incorporated herein by reference). In addition, a nucleic acid molecule encoding a FAP can be transferred into a variety of tissues using the particle bombardment method (Williams et al., *Proc. Natl. Acad. Sci., USA* 88:2726–2730 (1991), which is incorporated herein by reference). Such nucleic acid molecules can be linked to the appropriate nucleotide sequences required for transcription and translation.

A particularly useful mode of administration of a nucleic acid encoding a FAP is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promotor, an enhancer or other expression element specific for the desired subset of cells can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

An alternative method of modulating apoptosis in a cell is to introduce a nucleotide sequence encoding an antisense FAP or Fas into the cell and expressing the antisense nucleotide sequence in the cell. Such a nucleotide sequence can be introduced into and expressed in a cell using the methods and vectors described above. Chemically synthesized nucleotide sequences also can be administered directly to cells. Synthetic antisense oligonucleotides can be prepared using well known methods or can be purchased from commercial sources and, if desired, can incorporate nucleotide analogs to increase the resistance of the oligonucleotide to degradation by nucleases in a cell.

The present invention also provides methods for diagnosing a pathology that is characterized by an increased or decreased level of apoptosis in a cell to determine whether the increased or decreased level of apoptosis is due, for example, to increased or decreased expression of a FAP in the cell or to expression of a variant FAP. The identification of such a pathology, which can be due to altered association of a FAP and Fas in a cell, can allow for intervention therapy using an effective agent or a nucleic acid molecule or an antisense nucleotide sequence as described above. In general, a test sample can be obtained from a subject having a pathology characterized by increased or decreased apoptosis and can be compared to a control sample from a normal subject to determine whether a cell in the test sample has, for example, increased or decreased expression of FAP. The level of a FAP in a cell can be determined by contacting a sample with a reagent such as an anti-FAP antibody or Fas, either of which can specifically bind a FAP. For example, the level of a FAP in a cell can determined by well known immunoassay or immunohistochemical methods using an anti-FAP antibody (see, for example, Reed et al., supra, 1992; see, also, Harlow and Lane, supra, (1988)). As used herein, the term "reagent" means a chemical or biological molecule that can specifically bind to a FAP or to Fas or to a bound FAP-Fas complex. For example, either an anti-FAP antibody or Fas can be a reagent for a FAP, whereas either an anti-Fas antibody or a FAP can be a reagent for Fas.

As used herein, the term "test sample" means a cell or tissue specimen that is obtained from a subject and is to be examined for expression of a FAP in a cell in the sample. A test sample can be obtained, for example, during surgery or by needle biopsy and can be examined using the methods described herein to diagnose a pathology characterized by increased or decreased apoptosis. Increased or decreased expression of a FAP in a cell in a test sample can be determined by comparison to an expected normal level for a FAP in a particular cell type. A normal range of FAP levels in various cell types can be determined by sampling a statistically significant number of normal subjects. In addition, a control sample can be evaluated in parallel with a test sample in order to determine whether a pathology characterized by increased or decreased apoptosis is due to increased or decreased expression of a FAP. The test sample can be examined using, for example, immunohistochemical methods as described above or the sample can be further processed and examined. For example, an extract of a test sample can be prepared and examined to determine whether a FAP that is expressed in a cell in the sample can associate with Fas in the same manner as a FAP from a control cell or whether, instead, a variant FAP is expressed in the cell.

A diagnostic assay kit incorporating a reagent such as an anti-FAP antibody or Fas can be useful for detecting a pathology due to altered FAP expression in a cell. Such a kit is particularly useful because it allows for standardization of assay conditions. A kit can contain, in addition to a reagent, a reaction cocktail that provides suitable reaction conditions for performing the assay and a control sample that contains a known amount of a FAP. In addition, the kit can contain an antibody that is specific for the reagent.

A diagnostic assay should include a simple method for detecting the amount of a FAP in a sample that is bound to the reagent. Detection can be performed by labelling the reagent and detecting the presence of the label using well known methods (see, for example, Harlow and Lane, supra, 1988; chap. 9, for labelling an antibody). A reagent can be labelled with various detectable moieties including a radiolabel, an enzyme, biotin or a fluorochrome. Materials for labelling the reagent can be included in the diagnostic kit or can be purchased separately from a commercial source. Following contact of a labelled reagent with a test sample and, if desired, a control sample, specifically bound reagent can be identified by detecting the particular moiety.

A labelled antibody that can specifically bind the reagent also can be used to identify specific binding of an unlabelled reagent. For example, if the reagent is an anti-FAP antibody, a second antibody can be used to detect specific binding of the anti-FAP antibody. A second antibody generally will be specific for the particular class of the first antibody. For example, if an anti-FAP antibody is of the IgG class, a second antibody will be an anti-IgG antibody. Such second antibodies are readily available from commercial sources. The second antibody can be labelled using a detectable moiety as described above. When a sample is labelled using a second antibody, the sample is first contacted with a first antibody, then the sample is contacted with the labelled second antibody, which specifically binds to the first antibody and results in a labelled sample.

The following examples are intended to illustrate but not limit the invention.

EXAMPLE I

Identification of Fap's Using the Yeast Two Hybrid System

This example demonstrates the use of the yeast two hybrid system to identify cDNA sequences encoding proteins that can associate with the cytoplasmic domain of Fas.

A. Host/Vector Systems

Two different yeast host/plasmid vector systems, designated herein as the "EGY48 system" and the "IL40 system," were used to identify cDNA sequences encoding FAP's.

1. EGY48 system

In some experiments, S. cerevisiae strain EGY48 yeast cells were used as the host cells for the two hybrid assays ("EGY48 system"). Strain EGY48 cells have a MATα trp1 ura3 his3 LEU2::pLexAop6-LEU2 genotype. Yeast were grown in YPD medium. As indicated, strain EGY48 cells contain the Leu2 gene linked to the LexAOp and, therefore, can grow in leucine-deficient medium in the presence of a transcriptionally competent LexA DNA-binding domain.

The plasmids, pEG202 (FIG. 1) and pJG4-5 (FIG. 2), were used for expressing hybrid proteins in EGY48 yeast cells (Zervous et al., Cell 72:223–232 (1993); Gyuris et al., Cell 75:791–803 (1993); Golemis et al., In Current Protocols in Molecular Biology (ed. Ausubel et al.; Green Publ.; N.Y. 1994) each of which is incorporated herein by reference). Plasmid pEG202 was derived from plasmid LexA202+PL (Ruden et al., Nature 350:250–252 (1991); Ma and Ptashne, Cell 51:113–119 (1987), each of which is incorporated herein by reference) and contains additional unique polylinker sites for cloning. Plasmid pEG202 was created by cleaving LexA202+PL at the unique Sal I site, which is present in the polylinker downstream of LexA, and inserting a 22-mer that regenerates the Sal I site and also contains novel Nco I, Not I and Xho I sites.

Figure 1:
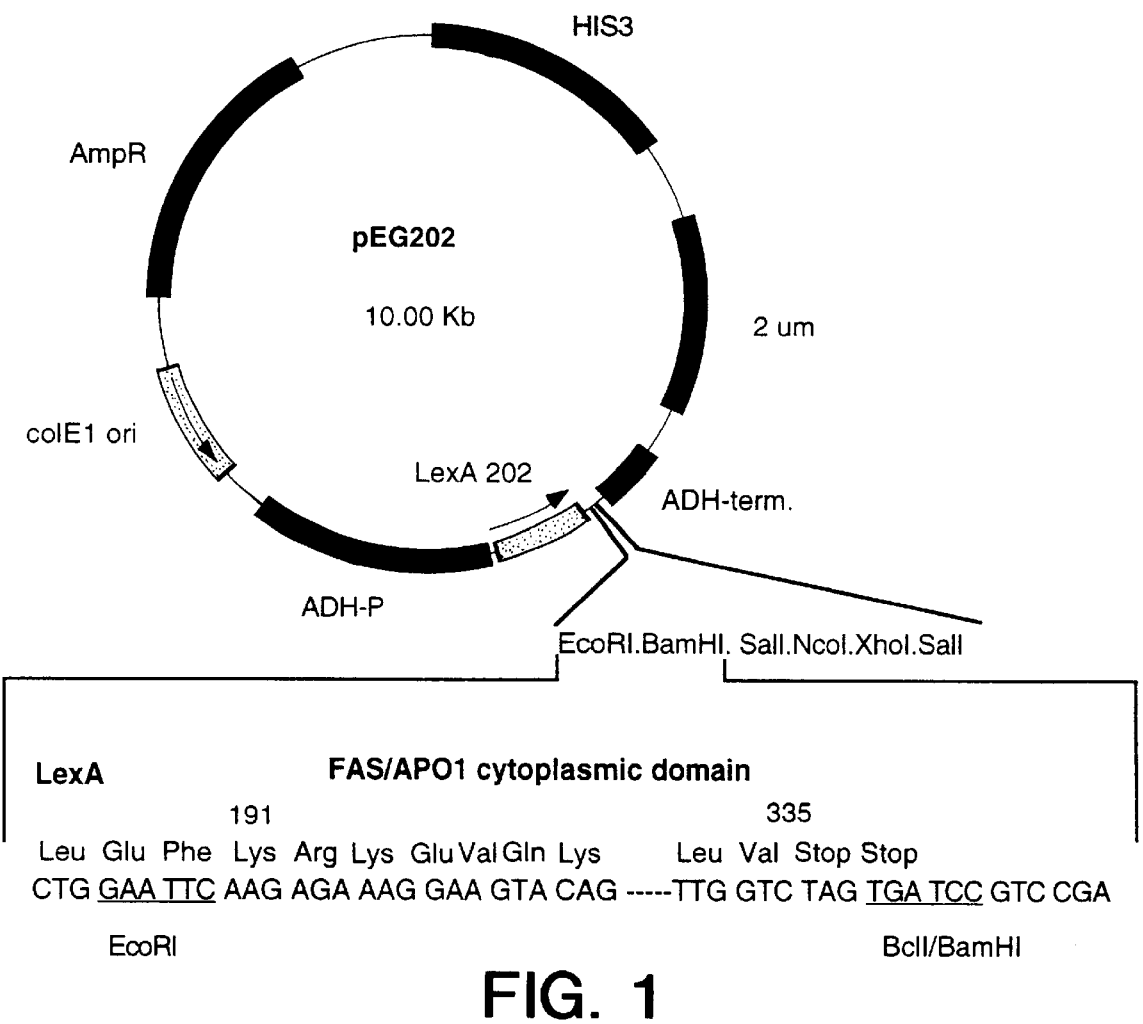
FIG. 1 provides a map of plasmid pEG202, which was used to produce LexA fusion proteins for use in the two hybrid assay system. pEG202 contains a gene that confers ampicillin resistance in bacteria (AmpR) and a colE1 origin of replication, which allows the plasmid to replicate in bacteria. The plasmid also contains a gene that allows a yeast cell containing the plasmid to grow in the absence of histidine (HIS3) and the yeast 2 micron origin of replication, which allows replication in yeast.

The 22-mer was constructed by synthesizing two oligonucleotides, 5'-TCGACCATGGCGGCCGCTCGAG-3' (SEQ ID NO: 7) and 5'-TCGACTCGAGCGGCCGCCATGG-3' (SEQ ID NO: 8) and allowing the complementary regions of the oligonucleotides to anneal. The 22-mer was ligated into the Sal I site of LexA202+PL to create pEG202. As shown in FIG. 1, pEG202 also contains the yeast 2 micron origin of replication and a histidine selectable marker. Expression of the LexA-fusion cassette is from the strong constitutive ADH1 promotor. Insertion of a cDNA encoding an open reading frame into the Eco RI, Bam HI, Sal I, Nco I, Not I or Xho I site of pEG202 results in the production of a LexA fusion protein.

The plasmid pJG4-5 was derived from a pUC plasmid and contains a galactose inducible promotor (FIG. 2). Insertion of the cDNA into the Eco RI or Xho I site results in the production of a fusion protein with the B42 transactivation domain and containing an SV40 nuclear localization signal and a hemagglutinin epitope tag (Zervous et al., supra, 1993; Gyuris et al., supra, 1993).

A β-gal reporter gene construct used in the EGY48 system was plasmid pSH18-34, which contains the lacZ gene linked to a LexA operator sequence (FIG. 3; Hanes and Brent, Cell 57:1275–1283 (1989); Hanes and Brent, Science 251:426–430 (1991), each of which is incorporated herein by reference). Plasmid pSH18-34, which contains 8 copies of the LexA operator sequence, was constructed by inserting two 78 base pair oligonucleotides formed by annealing (5'-
TCGACTGCTGTATATAAAACCAGTGGT-
TATATGTACAGTACTGCTGTATATAA AACCAGTGGTTATATGTACAGTACG-3'; SEQ ID NO: 9) and (5'-TCGAC GTACTGTACATATAACCACTG-GTTTTATATACAGCAGTACTGTACATATAACCACTG GTTTTATATACAGCAG-3'; SEQ ID NO: 10) into the Xho I site of plasmid pLR1Δ1 (West et al., *Mol. Cell. Biol.* 4:2467–2478 (1984), which is incorporated herein by reference). Each oligonucleotide contains four binding sites for the LexA DNA binding protein. A stably transformed strain EGY48 yeast cell line containing pSH18-34 was obtained based on its ability to grow in medium lacking uracil.

2. L40 system

In some experiments, *S. cervisiae* strain L40 yeast cells were used as the host cells for the two hybrid assay ("L40 system;" Vojtek et al., supra, 1993). Strain L40 cells have a MATa, trp1, leu2, his3, ade2, LYS2::(lexAop)4-HIS3, URA3::(lexAop)8-lacZ genotype and are stably transformed with histidine synthetase (HIS3) and lacZ reporter genes, both of which are under the control of a lexA operator. Strain L40 cells were grown in YPD medium.

The plasmids, pBMT-116 (FIG. 4) and pVP-16 (FIG. 5), were used in assays using strain L40 cells. Plasmid pBMT-116 encodes the LexA DNA-binding domain under control of an ADH promotor (FIG. 4). The presence of pBMT-116 in strain L40 cells permits the cells to grow in tryptophan-deficient medium. Plasmid pVP-16 encodes a trans-activating domain also under control of an ADH promotor (FIG. 5). The presence of pVP-16 in strain L40 cells permits the cells to grow in leucine-deficient medium.

B. Preparation of Vectors Encoding Hybrid Proteins

As a control and to eliminate false positive clones, a cDNA sequence encoding a Bcl-2 protein (from pSKII-bcl-2α; Tanaka et al., *J. Biol. Chem.* 268:10920–10926 (1993), which is incorporated herein by reference) was also modified by PCR mutagenesis (Higuchi et al., supra, 1990) using the primers described below and subcloned in frame into pEG202. In order to prevent potential targeting of expressed proteins to the nucleus, sequences corresponding to the transmembrane domain of Bcl-2 were deleted (Tsujimoto and Croce, *Proc. Natl. Acad. Sci., USA* 83:5214–5216 (1986), which is incorporated herein by reference) and a stop codon was inserted at the end of the open reading frame.

1. EGY48 system

The cDNA sequence encoding the cytoplasmic domain of human Fas (amino acids 191 to 335; see FIG. 6; Itoh et al., supra, 1991) was modified by PCR mutagenesis (Higuchi et al., In *PCR Protocols* (ed. Innes et al.; Academic Press; San Diego Calif. 1990), which is incorporated herein by reference) using the primers described below and subcloned in frame into pEG202 to produce pEG/Fas(191–335). As described above, pEG202 utilizes an ADH promoter to constitutively drive expression of a fusion protein containing an N-terminal LexA DNA binding domain. The cDNA sequence for the cytoplasmic domain of human Fas was subcloned into the Eco RI site of pEG202, in-frame with the upstream LexA sequences. Forward and reverse primers, which contained an Eco RI site (underlined) or BclI site (italics), were as follows (bold indicates DNA encoding stop codon; TCA): (i) Fas (amino acids (aa) 191 to 335) (5'-G<u>GAATTC</u>AAGAGAAAGGAAGTACAG-3'; SEQ ID NO: 11) and (5'-*TGATCA*CTAGACCAAGCTTTGGAT-3'; SEQ ID NO: 12); (ii) Bcl-2 (aa 1 to 218) (5'-G<u>GAATTC</u>ATGGCGCACGCTGGGAGAAC-3'; SEQ ID NO: 13) and (5'-*TGATCA*CTTCAGAGACAGCCAC-3'; SEQ ID NO 14).

The pJG4-5 plasmid utilizes a galactose-inducible promoter (GAL1-p) to inducibly drive expression of fusion proteins containing an N-terminal B42 trans-activation domain (FIG. 2). B42 fusion proteins encoding candidate FAP's were produced by cloning a HeLa cell cDNA library into the Eco RI or Xho I sites of pJG4-5 (pJG/HeLa).

2. L40 system

The cDNA sequences encoding the various fragments of the cytoplasmic domain (Itoh et al., supra, 1991) were generated by PCR (Higuchi et al., supra, 1990) using the forward (F) and reverse (R) primers containing Eco RI (underlined) and Bcl I (italics) sites (bold indicates STOP codon, TCA), as follows: 1) 5'-G<u>GAATTC</u>AAGAGAAAGGAAGTACAG-3' (F1; SEQ ID NO: 11); 2)5'-G<u>GAATTC</u>AAAGGCTTTGCTTCGAAAG-3' (F2; SEQ ID NO: 15); 3)5'-GTGATCACGCTTCTTTCTTTCCATG-3' (R1; SEQ ID NO: 16); and 4)5'-GTGATCACTAGACCAAGCTTTGGAT-3' (R2; SEQ ID NO: 12). Use of the following combinations of primers produced the indicated Fas fragments: 1) F1+R2=Fas (191–335); 2) F1+R1=Fas(119–290); 3)F2+R1=Fas (246–335); and 4) F2+R2=Fas(246–290). Fas(321–335) was generated by restriction endonuclease digestion using SpeI and filled-in using T4 DNA polymerase to generate a STOP codon. The sequence encoding Fas(119–335) was subcloned in frame into pBMT-116 to produce pBMT/Fas(191–335)

The pVP-16 plasmid utilizes an ADH promotor to drive expression of fusion proteins containing the VP-16 trans-activation domain. A cDNA library was prepared by random primed synthesis of 9.5–10.5 day CD1 mouse embryo poly-A⁺ mRNA using phosphorylated hexamers. The ratio of primer to template was adjusted to encourage multiple synthesis reactions per RNA molecule, thus generating an average first strand size of about 500 nucleotides. Following second strand synthesis with RNAse H, DNA polymerase I and *E. coli* DNA ligase, the cDNA was repaired using T4 DNA polymerase and the following linker was attached:

5'-ATCCTCTTAGACTGCGGCCGCTCA-3' (SEQ ID NO: 17)

3'-GAGAATCTGACGCCGGCGAGT-5'PO$_4$ (SEQ ID NO: 18).

The reaction products were fractionated by agarose gel electrophoresis and DNA fragments of 350 to 700 nucleotides were collected. The DNA fragments were extracted through a Millipore filter column, then phenol:chloroform (1:1) extracted and ethanol precipitated. To generate large quantities of cDNA, the size-selected DNA was amplified using the sense primer (SEQ ID NO: 9)from above in the presence of 5 mM Mg$^{+2}$. Following amplification to near saturation, the reaction was diluted 10× and amplification was continued for one additional cycle. Incorporation of radiolabeled nucleotide indicated an amplification efficiency of 1.9 per cycle. Initial amplifiable cDNA was estimated to total more than 1×10$^8$ molecules. The amplified DNA was incubated overnight with 10 units Not I/μg DNA, then cloned into pVP-16 (pVP/embryo; Vojtek et al., supra, 1993)).

For sequencing Not I inserts in pVP-16, the cDNA insert is flanked by an eleven nucleotide palindrome, nine of which form GC base pairs. These inserts can be sequenced using a sense primer (5'-GGTACCGAGCTCAATTGCGG-3'; SEQ ID NO: 19), which covers part of the Not I palindrome. Alternative, sequencing can be performed at an elevated temperature using Taq DNA polymerase.

C. Assay Methods

Plasmid DNA was transformed into yeast cells by the LiCl method or by the LiOAc method (Ito et al.,*J. Bacteriol.* 153:163–168 (1983); Gietz et al., *Nucl. Acids Res.* 20:1425

(1992); Schiestl et al., *Curr. Genet.* 16:339–346 (1989), each of which is incorporated herein by reference). In experiments using the EGY48 system, transformed cells were grown in complete minimal medium lacking uracil, tryptophan or histidine as necessary to select for the presence of pSH, pJG or pEG derived plasmids, respectively. In addition, growth in leucine-deficient medium indicated formation of a transcriptionally active LexA/B42 complex. In experiments using the L40 system, transformed cells were grown in complete minimal medium lacking tryptophan or leucine as necessary to select for the presence of pBMT or pVP derived plasmids, respectively. In addition, growth in histidine-deficient medium indicated formation of transcriptionally active LexA/VP16 complex.

1. EGY48 system

Following expression of various fusion proteins, yeast cell extracts were prepared using a spheroplast method (Smith and Corcoran, In *Current Protocols in Molecular Biology* (ed. Ausubel et al., Green Publ.; N.Y. 1989), which is incorporated herein by reference) and expression of LexA- or B42-fusion proteins was confirmed by immunoblot assays using a polyclonal anti-LexA antiserum, which can be prepared as described by Brent and Ptashne (*Nature* 312:612–615 (1984), which is incorporated herein by reference) or an anti-HA1 monoclonal antibody (clone 12CA5; Boehringer Mannheim; Indianapolis Ind.), respectively.

EGY48 yeast cells were stably transformed with pSH18-34, which expresses the reporter lacZ gene from a lexA operator. The cells then were transformed with pEG/Fas (191–335) and selected for growth in minimal medium lacking histidine. The selected colonies were transformed with pJG/HeLa cDNA library and plated on medium lacking histidine, leucine and tryptophan to identify cloned cDNA sequences that encoded candidate FAP's.

Approximately 1.7×10⁷ colonies were plated to each of 20 plates. Of the 17 million yeast transformants screened using the entire cytoplasmic domain of Fas, approximately 1210 independent colonies of cell were a Leu⁺ phenotype. Four replicas were made from all 1210 Leu⁺ transformants and plated as follows: 1) glucose, X-gal, leucine; 2) galactose, X-gal, leucine; 3) glucose; and 4) galactose plates. Eighty-five transformants grew on leucine-deficient medium and exhibited galactose-inducible β-gal activity.

Twenty-seven clones were selected and were "cured" of LexA/Fas-encoding plasmids by growing the cells in histidine-containing medium. The cured cells then were mated against a panel of a-type yeast (strain RFY206 {Mata, ura3, trp1, leu2}) containing various plasmids that produced either LexA/Fas, LexA/Ras, LexA/CD40, LexA/Bcl-2 (short) or LexA/lamin (see, Vojtek et al., supra, 1993; Bartels et al., *Biotechniques* 14:920–924 (1993), which is incorporated herein by reference) fusion protein. The mated cells were selected for growth in medium lacking histidine and tryptophan to obtain cells that contained both a pJGHeLa clone and a LexA-fusion protein. Fifteen clones were partially sequenced and analyzed for homology by performing a database search. Four clones were identical to the nucleic acid sequence encoding the 78 kDa glucose regulated protein GRP78 (not shown; Ting and Lee, supra, 1988).

2. L40 system

The pBMT/Fas(119–335) plasmid was introduced into L40 cells, which contain histidine synthetase (HIS3) and β-galactosidase (lacz; β-gal) reporter genes under the control of lexA operators. The resulting transformants were selected for ability to grow on medium lacking tryptophan, since the pBMT-116 plasmid contains a TRP1 gene that complements the defect in the host strain. L40 cells containing the pBMT/Fas(191–335) then were transformed with the pVP-16/embryo cDNA library. Transformants were selected by growth on plates lacking leucine, based on the presence of a LEU2 gene in the pVP-16 vector.

Colonies expressing a cDNA sequence encoding a candidate FAP were identified initially by their ability to grow in medium lacking histidine due to expression of the lexAop/HIS3 reporter gene construct in these yeast cells. Approximately 300 million transformants were screened and 395 His+ colonies were identified. These 395 clones were examined further using a β-gal colorimetric filter assay (Breeden & Nasmyth, *Cold Sprina Harb. Symp. Ouant. Biol.* 50:643–650 (1985), which is incorporated herein by reference) to identify expression of the lacZ reporter gene, which is under the control of a lexA operator. Following this second screening procedure, 84 positive clones were obtained.

The 84 clones were cured of LexA/Fas-encoding plasmids by growing the cells in tryptophan-containing medium. The cured cells then were mated against a panel of a-type yeast (strain NA-8711-A {a, leu2, his3, trp1, pho3, pho5}) plasmids containing various fusion proteins as described above for the EGY48 system. The mated cells were selected for growth in medium lacking tryptophan and leucine to obtain cells that contained both a pVP\embryo clone and a LexA-fusion protein.

Of the 84 clones selected, two reacted specifically with the LexA/Fas protein, as determined by the β-gal filter assay (Breeden and Nasmyth, supra, 1985). DNA sequence analysis of the two clones revealed inserts of approximately 350 base pairs (bp; pVP16-31) and 380 bp (pVP16-43; see FIG. 7). Alignment of these mouse cDNA clones with each other demonstrated that they represented overlapping independent cDNA sequences. The cDNA clones were sequenced and a database search revealed greater than 95% homology with a human cDNA sequence encoding the protein tyrosine phosphatase, PTP-BAS. In particular, the cDNA sequences were homologous with the second GLGF repeat in PTP-BAS (FIG. 7). As described in Example II.C., below, the cDNA inserts obtained using the two hybrid system were used to screen a lambda phage human cDNA library.

The pVP16-31 plasmid was cointroduced into L40 cells with a pBMT-116 plasmid containing nucleic acid sequences encoding various fragments of Fas (see FIG. 8) and transcriptional activation from the lacZ gene was assayed using the β-gal filter assay (Breeden and Nasmyth, supra, 1985). As shown in FIG. 8, fragments of Fas that included the C-terminal 15 amino acids of Fas were able to bind the polypeptide encoded by the cDNA insert in pVP16-31 and, as a result, activate transcription of the lacZ reporter gene.

EXAMPLE II

In Vitro Assays To Identify A FAP

This example describes methods for constructing fusion proteins useful for detecting and characterizing a FAP in vitro.

A. Production of GST/Fas Fusion Proteins

A cloning vector containing the FLAG™ peptide, an enterokinase recognition site and heart muscle kinase (HMK) substrate domain based on pGEX-2TX (FIG. 9; Pharmacia; Piscataway N.J.) was used for construction of GST/Fas fusion proteins (FIG. 6). This vector contains an inducible tac promoter, the glutathione-S-transferase (GST) gene from *Schistosoma japonicum*, a multiple cloning site, the FLAG™ peptide for immunological detection and purification, a thrombin and enterokinase cleavage site located between the GST gene and the multiple cloning site and the HMK kinase domain for radiolabeling the fusion proteins (see below).

A series of GST/Fas fusion proteins was produced in *E. coli* using pGEX-2TX (see FIGS. 6 and 8). The nucleic acid sequences encoding the various Fas fragments described above were subcloned into pBluescript™ (Stratagene; San Diego Calif.) or were directly cloned into pGEX-2TX plasmid. The nucleic acid molecules encoding the GST/Fas fusion proteins were sequenced using a Sequenase version 2.0 kit (U.S. Biochemical; Cleveland Ohio) to confirm that the reading frame was correct and that no erroneous nucleotides were introduced during PCR amplification. The GST-fusion proteins contained the following segments of the Fas cytoplasmic domain: (A) amino acid residues 191–335, which corresponding to the entire cytoplasmic domain (GST/Fas(191–335)); (B) residues 191–290, which represent the region extending from the transmembrane domain to the end of the conserved region (GST/Fas(191–290)); (C) residues 246–335, which is a region from the beginning of the conserved region to the C-terminus of Fas (GST/Fas (246–335)); (D) residues 246–290, which contains the region of Fas that is conserved among the members of the TNFR family of proteins (GST/Fas(246–290)); (E) residues 191–320, which contains the entire cytoplasmic domain, except the C-terminal 15 amino acids (GST/Fas(191–320)) and F) residues 321–335, which represent the C-terminal amino acids of Fas that constitute a negative regulatory domain (GST/Fas(321–335); FIG. 6).

The GST/Fas fusion proteins were expressed in *E. coli* by inducing expression from the tac promoter with 1 mM IPTG. Approximately 1–10 μg GST/Fas fusion protein was obtained from a 1 ml bacterial culture. The GST/Fas fusion proteins were partially purified from bacterial lysate by affinity chromatography on glutathione-Sepharose 4B (Sigma; St. Louis Mo.). Analysis of the GST/Fas fusion proteins by SDS-PAGE and Coomassie blue staining confirmed that the fusion proteins purified from *E. coli* lysates had the expected molecular weight (not shown).

In some experiments, a $^{32}$P-labelled GST/Fas fusion protein is used to detect the presence of a FAP. A $^{32}$P-GST/Fas is generated using bovine heart muscle kinase (Sigma). Briefly, GST/Fas is immobilized by binding to a glutathione-Sepharose column. The bound GST/Fas is washed with 1× HMK buffer (20 mM Tris-HCl, pH 7.5, 100 mM NaCl, 12 mM MgCl$_2$) and the coated beads are resuspended in 2–3 bead volumes (vol) of 1× HMK buffer containing a 1 unit/ml catalytic subunit of cAMP-dependent protein kinase (Sigma), 1 mCi/ml γ[$^{32}$P]-ATP (6000 Ci/mmol, 10 mCi/ml; Dupont/NEN; Boston Mass.) and 1 mM dithiothreitol (DTT). The kinase reaction is allowed to proceed at room temperature (RT)for 60 min, then stopped by the addition of 1 ml HMK stop buffer (10 mM sodium phosphate, pH 8.0, 10 mM sodium pyrophosphate, 10 mM EDTA, 1 mg/ml BSA). Free γ[$^{32}$P]-ATP is removed by resuspending the reaction mixture in stop buffer, pelleting the glutathione Sepharose beads by centrifugation and removing the buffer; these steps are repeated 4×, then the Sepharose beads are washed at least 5× with HMK buffer. After washing, the beads are resuspended in elution buffer (5 mM glutathione, 50 mM Tris-HCl, pH 8.0, 120 mM NaCl) and stored at 4° C.

B. Identification of FAP's in Various Tissues

Far western blotting (ligand blotting) was used to detect the presence of FAP's in various cell types. In one experiment, 50 μg total protein from mouse S49 T cells were analyzed. Proteins were obtained by lysing the cells in 10 mM Tris, pH 7.4, 150 mM NaCl, 0.1% SDS, 1% sodium deoxycholate, 1% Triton X-100 and protease inhibitors as described by Reed et al., *Canc. Res.* 51:6529–6538 (1991), which is incorporated herein by reference, then fractionated by electrophoresis on a 12% SDS-polyacrylamide gel. Following electrophoresis, the proteins were transferred to nitrocellulose and the nitrocellulose filter was processed by a series of denaturation/renaturation steps. The filters were incubated with HBB buffer (20 mM Hepes, pH 7.5, 5 mM MgCl$_2$, 1 mM KCl, 5 mM DTT) containing 6M guanidine-HCl to denature the proteins. After 10 min incubation with gentle shaking, the solution was removed and the same procedure was repeated a second time. After 10 min, the solution was removed and the filters were then incubated sequentially with HBB buffer containing 3M guanidine-HCl, 1.5M guanidine-HCl, 0.75M guanidine-HCl and 0.38M guanidine-HCl for 5 min each, followed by a 30 min incubation with shaking in HBB buffer containing 5% skim milk. The solution was removed and replaced with HBB buffer containing 1% skim milk and shaking was continued for 10 min. The filters were then incubated overnight in a solution of HBB containing 1% skim milk and 1 μg/ml GST/Fas(191–335), which contains the entire Fas cytoplasmic domain, or GST (control).

Following incubation, the filters were washed 3× with PBST buffer (137 mM NaCl, 2.76 mM KCl, 4.3 mM KNa$_2$HPO$_4$, 0.2% triton X-100) for 15 min, then transferred to a solution containing 1:1000 dilution of a mouse anti-GST monoclonal antibody (GS7; Santa Cruz Biotechnology; Santa Cruz Calif.) in phosphate buffered saline. The filters were incubated with gentle shaking for 2 hr at RT, then were washed 3× with PBST for 10 min. Following washing, the filters were soaked in 3 ml anti-mouse IgG-alkaline phosphatase (1 mg/ml; 1:7000 dilution; Promega; Madison Wis.) for 1 hr at RT, then washed 3× with PBST buffer and color development of the complexes was performed using NBT/BCIP (nitroblue tetrazolium/5-bromo-4,chloro-3-indolylphosphate).

As a preliminary attempt to identify FAS/APO-1 binding proteins, GST/Fas fusion protein containing the entire cytoplasmic domain of Fas was purified by affinity chromatography and radiolabeled in vitro using γ$^{32}$P-ATP and the catalytic subunit of cAMP-kinase. The $^{32}$P-GST/Fas was incubated with the protein blots. At least three FAP's having molecular weights of 32, 30 and 18 kDa were identified in the mouse S49 T cell protein extracts (FIG. 10). No band corresponding to the 36 kDa Fas protein was detected. Similar sized FAP's also were detected in human breast (MCF7), ovarian (A278), lung (H460) and colon (Caco-2) cancer cell lines and in normal mouse T cells and a mouse B cell lymphoma line (RS11846) (not shown).

2. Screening a cDNA expression library $^{32}$P-labeled GST/Fas protein can be used for direct screening of a λgt11 cDNA expression library, which can be obtained from a commercial source (Clontech; Palo Alto Calif.) or constructed using well known methods (Sambrook et al., supra, 1989). Radiolabeled GST and GST/Fas is obtained as described above. Phage are transferred to nitrocellulose filters, which are placed in a plastic bag. Hybridization buffer (1% milk, 20 mM Hepes-KOH, pH 7.7, 75 mM KCl, 0.1 mM EDTA, 2.5 mM MgCl$_2$) is added and approximately 250,000 cpm/ml GST/Fas (or GST) are added. Filters are incubated at 4° C., overnight, in the presence of a 20-fold molar excess of unlabeled GST protein (see, for example, Kaelin et al., supra, 1992).

Positive plaques are selected and subjected to further rounds of screening as above. After 3–4 rounds of screening, the cDNA inserts of plaque purified phages are amplified by PCR using primers that flank the vector cloning site or, alternatively, are liberated from the phage by restriction digestion of purified phage DNA. These cDNA sequences are subcloned into the Eco RI site of the pET vector, pET5c (Novagen; Madison Wis.), which produces T7/Protein 10 fusion proteins that are in frame with the inserted cDNA. Expression of the recombinant proteins is induced in E. coli using IPTG, fractionated by SDS-PAGE and transferred to nitrocellulose filters. The resulting blots are analyzed using the far western method as described above using the same GST/Fas fusion protein that originally was used to screen the library. Clones that produce FAP's, which bind the GST/Fas probe, are sequenced and their amino-acid sequences are deduced. These sequences are checked against nucleotide and protein databases to identify novel or previously described proteins.

Positive CDNA sequences obtained through the protein interaction cloning technique described above are used to produce hybridization probes to screen various tissues by northern blot analysis. Appropriate clones are then used as hybridization probes to screen commercially-available lambda phage cDNA libraries prepared from an appropriate tissue to obtain a cDNA encoding the entire open reading frames for various FAP's. Alternatively, 5'- or 3'-RACE methods can be used to directly amplify the regions of the cDNA from reverse transcribed RNA (Frohman et al., Proc. Natl. Acad. Sci., USA 85:8998–9002 (1988), which is incorporated herein by reference).

C. Characterization of FAP binding to Fas

The ability of a FAP identified using the yeast two hybrid system as described above to associate with the GST/Fas fusion proteins was examined. The cDNA sequence in HFAP10 was subcloned into the Bluescript vector, pSK-II (Stratagene), and was translated in vitro from an internal methionine codon in the presence of $^{35}$S-L-methionine using a coupled in vitro transcription/translation system (TNT lysate; Promega) and T7 RNA polymerase. The $^{35}$S-labeled protein was incubated with various GST/Fas fusion proteins, which had been immobilized on glutathione-Sepharose beads in buffer A (150 mM NaCl, 50 mM Tris, pH 8.0, 5 mM DTT, 2 mM EDTA, 0.1% NP-40, 1 mM phenylmethylsulfonyl fluoride, 1 μg/ml leupeptin) for 16 hrs at 4° C. Following incubation, the beads were washed vigorously 10× in buffer A and bound proteins were recovered with the glutathione-Sepharose beads by centrifugation, eluted into boiling Laemmli buffer and analyzed by SDS-PAGE and fluorography.

The polypeptide derived from the human PTP-BAS bound specifically to GST/Fas(191–335), which contains the entire Fas cytoplasmic domain, to GST/Fas(246–335), which contains the conserved region of Fas to the C-terminus and to GST/Fas(321–335), which contains the C-terminal 15 amino acids of Fas (FIG. 8; "In vitro binding assay"). In contrast, the polypeptide did not bind to GST/Fas fusion proteins containing the conserved region, alone, to the region of Fas beginning from the transmembrane domain to the end of the conserved region, to GST, alone, to either of two forms of the TNFR or to CD40 (not shown). These results correlate with the results of the two hybrid assay described above and indicate that the C-terminal 15 amino acids of Fas are sufficient for the association of Fas with a FAP such as PTP-BAS and that FAP's associate specifically with Fas, but not other members of the TNFR family.

EXAMPLE III

Characterization of PTP-BAS Type 4 and PTP-BAS Type 5a

This example describes the characteristics of human PTP-BAS type 4 and human PTP-BAS type 5a.

Clones pVP16-31 and pVP16-41 (see above) were used as hybridization probes to screen a human fetal brain cDNA library prepared in lambda gt11 (Clontech) and a mouse liver cDNA library (see Example IV). From the human cDNA library, two clones were obtained (FIG. 7; HFAP10 and HFAP20 ). The cDNA inserts were sequenced as described above and the amino acid sequences were deduced (see FIGS. 12 and 14). The polypeptides encoded by these cDNA sequences were designated PTP-BAS type 4 and PTP-BAS type 5a, respectively.

HFAP10 contained an 1814 nucleotide insert (FIG. 13; SEQ ID NO: 2), which encoded 604 amino acids of PTP-BAS type 4 (FIG. 12; SEQ ID NO: 1). As shown in FIG. 11, the amino acid sequence of PTP-BAS type 4 comprises amino acids 1279–1883 relative to the amino acid residues of PTP-BAS type 1. This amino acid sequence of PTP-BAS type 4 includes GLGF2, GLGF3 and GLGF4. In addition, PTP-BAS type 4 includes a 5 amino acid VLFDK insert in GLGF2.

HFAP20 contained an approximately 1500 nucleotide insert, of which about 600 nucleotides have yet to be determined (FIG. 15; SEQ ID NO: 4 and SEQ ID NO:22). The nucleotide sequence of HFAP20 encoded a 92 amino acid polypeptide. The N-terminal 68 amino acids of the polypeptide encoded by HFPA20 are homologous to PTP-BAS and, therefore, the polypeptide has been designated PTP-BAS type 5a (FIG. 14; SEQ ID NO: 3). As shown in FIG. 11, the amino acid sequence of PTP-BAS type 5a comprises amino acids 1377–1445 relative to the amino acid residues of PTP-BAS type 1 and includes a GLGF2, which, like PTP-BAS type 4, contains a 5 amino acid VLFDK (SEQ ID NO:21) insert in GLGF2. The remaining 24 C-terminal amino acids in the PTP-BAS type 5a polypeptide are not homologous to the other members of the PTP-BAS family of proteins, including PTP-BAS type 4 (see FIG. 11). Significantly, the amino acid sequence is terminated by a STOP codon, TGA, (nucleotides 4408–4410 in FIG. 15). As a result, PTP-BAS type 5a does not contain a catalytic phosphatase domain (see FIG. 11). As described below, human PTP-BAS type 5a is a member of a subfamily of PTP-BAS type 5 proteins, which do not contain a catalytic phosphatase domain.

EXAMPLE IV

Identification and Characterization of Mouse PTP-BAS TYPE 5b

This example describes the identification and characterization of mouse PTP-BAS type 5b, which is a member of the subfamily of PTP-BAS type proteins using the yeast two hybrid system.

The cDNA inserts from plasmids pVP16-31 and pVP16-43 were used to screen a mouse liver cDNA library, which was cloned in lambda gt11 (Clontech). A cDNA clone was obtained that contained an insert encoding a mouse FAP, MFAP23 (FIG. 11). A partial nucleotide sequence for MFAP23 is shown in FIG. 17 (SEQ ID NO: 6) and the deduced amino acid sequence is shown in FIG. 16 (SEQ ID NO: 5).

As shown in FIG. 11, the N-terminus of the amino acid sequence encoded by MFAP23 is homologous with the amino acid sequence of a PTP-BAS beginning with amino acid residue 1180 in the human PTP-BAS type 1 protein. The mouse PTP-BAS contains GFLG2, GLGF3, GLGF4 and GLGF5 repeats. However, like human PTP-BAS type 5a, the mouse PTP-BAS type 5b protein diverges at its C-terminus and terminates due to a STOP codon (see FIGS. 11, 16 and 17). As a result, the mouse PTP-BAS type 5b does not contain a catalytic phosphatase domain. Thus, the mouse PTP-BAS is another example of a member of a subfamily of PTP-BAS type 5 proteins, which do not contain a catalytic phosphatase domain.

EXAMPLE V

PTP-BAS Expression Reduces Apoptosis

This example demonstrates that the level of apoptosis is correlated to the expression of a FAP in the cell.

A. Sensitivity to anti-Fas antibody-induced apoptosis is correlated to endogenous PTP-BAS expression in the cell Various tumor cell lines, including SNG-M cells, Jurkat cells, HepG2 cells, Raji cells, RS11846 cells, 380 cells and Cos7 cells, were examined for PTP-BAS expression and the sensitivity of the cell lines to apoptosis induced by exposure of the cells to anti-Fas antibody was determined. All of the cell lines, except the Cos7 cells, expressed Fas antigen as determined by flow cytometric immunofluroescence assay using an anti-Fas antibody and by northern blot analysis (see FIG. 18). Cos7 cells were transfected with a Fas cDNA to produce Cos7-Fas cells, which expressed Fas antigen (Oehm et al., J. Biol. Chem. 267:10709–10715 (1992), which is incorporated herein by reference).

The presence or absence of PTP-BAS mRNA in the tumor cell lines was determined by northern blot analysis. Briefly, 20 μg total RNA was isolated from each cell line, separated by electrophoresis, transferred to a nylon filter and hybridized with a $^{32}$P-labelled HFAP10 probe (see Example III). Of the tumor cells lines examined, SNG-M, Jurkat, HepG2 and Raji cells had no detectable PTP-BAS mRNA, whereas RS11846, 380 and Cos7 cells expressed PTP-BAS mRNA (FIG. 18).

$2\times10^5$ cells/ml were cultured for 24 hr in the presence (+) or absence (−) of 1 μg/ml anti-Fas antibody (CH11; Medical and Biological Laboratories; Nagoya Japan) and cell viability was determined by trypan blue exclusion. As shown in FIG. 18, the RS11846 cells, 380 cells and Cos7-Fas cells, which expressed PTP-BAS mRNA, were completely resistant to apoptosis induced by anti-Fas antibody. In contrast, cells lacking PTP-BAS mRNA were sensitive to various extents to anti-Fas antibody-induced apoptosis. These results demonstrate that expression of PTP-BAS in a cell renders the cell relatively resistant to Fas-induced apoptosis.

B. Expression of exogenous human PTP-BAS type 4 in a cell confers resistance to apoptosis A cDNA encoding the full length human PTP-BAS type 4 protein was constructed by a series of four overlapping PCR reactions using DNA obtained from the lambda gt11 fetal brain cDNA library (see Example III). The 5'- and 3'-flanking primers contained Not I sites that were used for subdloning downstream of the cytomegalovirus (CMV) promotor in pRc/CMV, which contains a G418 resistance gene (Invitrogen; San Diego Calif.). Jurkat cells, which do not express detectable levels of endogenous PTP-BAS (see FIG. 18), were electroporated with 25 μg pRc/CMV or pRc/CMV-PTP-BAS 4, stable transfectants were obtained by G418 selection (0.8 mg/ml) and independent clones were isolated by limiting dilution.

Relative levels of PTP-BAS type 4 of the cloned cells were determined by northern blot analysis (see FIG. 19). Cloned cells were incubated 4 hr in the presence or absence of 50 ng/ml anti-Fas antibody, then analyzed using the TUNEL assay, which measures DNA fragmentation indicative of apoptosis (see Gorczyca et al., Canc. Res. 53:1945 (1993), which is incorporated herein by reference). As shown in FIG. 19, the relative resistance to anti-Fas antibody-induced apoptosis was correlated to the amount of PTP-BAS type 4 expressed in the cloned cell lines. Furthermore, clones expressing higher levels of PTP-BAS type 4 withstood higher concentrations of antibody as compared to control cells and remained viable for longer periods time (not shown).

A cDNA encoding a C-terminal truncated PTP-BAS type 4 protein was created by introducing a STOP codon after position 2225. The cDNA encoding full length or truncated PTP-BAS type 4 were cloned into pREP-9 (Invitrogen) and expressed in Jurkat cells, then the transfected cells were examined for sensitivity to anti-Fas antibody-induced apoptosis. Cloned cells expressing the truncated PTP-BAS type 4 protein, which lacks the catalytic domain, were not protected from Fas-induced DNA degradation (not shown). These results demonstrate that the level of Fas-induced apoptosis in a cell can be regulated by expression of a PTP-BAS in the cell and that the PTP-BAS phosphatase activity is required for this regulation.

Although the invention has been described with reference to the examples above, it should be understood that various modifications can be made without departing from the spirit of the invention. Accordingly, the invention is limited only by the following claims.

---

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 610 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
His  Gly  Ser  Pro  Ser  Pro  Ser  Val  Ile  Ser  Lys  Ala  Thr  Glu  Lys  Glu
 1              5                        10                       15
```

| | | | | | | | | | | | | | | |
|---|---|---|---|---|---|---|---|---|---|---|---|---|---|---|
| Thr | Phe | Thr | Asp<br>20 | Ser | Asn | Gln | Ser | Lys<br>25 | Thr | Lys | Lys | Pro | Gly<br>30 | Ile | Ser |
| Asp | Val | Thr<br>35 | Asp | Tyr | Ser | Asp | Arg<br>40 | Gly | Asp | Ser | Asp | Met<br>45 | Asp | Glu | Ala |
| Thr | Tyr<br>50 | Ser | Ser | Ser | Gln | Asp<br>55 | His | Gln | Thr | Pro | Lys<br>60 | Gln | Glu | Ser | Ser |
| Ser<br>65 | Ser | Val | Asn | Thr | Ser<br>70 | Asn | Lys | Met | Asn | Phe<br>75 | Lys | Thr | Phe | Ser | Ser<br>80 |
| Ser | Pro | Pro | Lys | Pro<br>85 | Gly | Asp | Ile | Phe | Glu<br>90 | Val | Glu | Leu | Ala | Lys<br>95 | Asn |
| Asp | Asn | Ser | Leu<br>100 | Gly | Ile | Ser | Val | Thr<br>105 | Val | Leu | Phe | Asp | Lys<br>110 | Gly | Gly |
| Val | Asn | Thr<br>115 | Ser | Val | Arg | His | Gly<br>120 | Gly | Ile | Tyr | Val | Lys<br>125 | Ala | Val | Ile |
| Pro | Gln<br>130 | Gly | Ala | Ala | Glu | Ser<br>135 | Asp | Gly | Arg | Ile | His<br>140 | Lys | Gly | Asp | Arg |
| Val<br>145 | Leu | Ala | Val | Asn | Gly<br>150 | Val | Ser | Leu | Glu | Gly<br>155 | Ala | Thr | His | Lys | Gln<br>160 |
| Ala | Val | Glu | Thr | Leu<br>165 | Arg | Asn | Thr | Gly | Gln<br>170 | Val | Val | His | Leu | Leu<br>175 | Leu |
| Glu | Lys | Gly | Gln | Ser<br>180 | Pro | Thr | Ser | Lys | Glu<br>185 | His | Val | Pro | Val<br>190 | Thr | Pro |
| Gln | Cys | Thr<br>195 | Leu | Ser | Asp | Gln | Asn<br>200 | Ala | Gln | Gly | Gln | Gly<br>205 | Pro | Glu | Lys |
| Val | Lys<br>210 | Lys | Thr | Thr | Gln | Val<br>215 | Lys | Asp | Tyr | Ser | Phe<br>220 | Val | Thr | Glu | Glu |
| Asn<br>225 | Thr | Phe | Glu | Val | Lys<br>230 | Leu | Phe | Lys | Asn | Ser<br>235 | Ser | Gly | Leu | Gly | Phe<br>240 |
| Ser | Phe | Ser | Arg | Glu<br>245 | Asp | Asn | Leu | Ile | Pro<br>250 | Glu | Gln | Ile | Asn | Ala<br>255 | Ser |
| Ile | Val | Arg | Val<br>260 | Lys | Lys | Leu | Phe | Pro<br>265 | Gly | Gln | Pro | Ala | Ala<br>270 | Glu | Ser |
| Gly | Lys | Ile<br>275 | Asp | Val | Gly | Asp | Val<br>280 | Ile | Leu | Lys | Val | Asn<br>285 | Gly | Ala | Ser |
| Leu | Lys<br>290 | Gly | Leu | Ser | Gln<br>295 | Gln | Glu | Val | Ile | Ser<br>300 | Ala | Leu | Arg | Gly | Thr |
| Ala<br>305 | Pro | Glu | Val | Phe | Leu<br>310 | Leu | Leu | Cys | Arg | Pro<br>315 | Pro | Pro | Gly | Val | Leu<br>320 |
| Pro | Glu | Ile | Asp | Thr<br>325 | Ala | Leu | Leu | Thr | Pro<br>330 | Leu | Gln | Ser | Pro | Ala<br>335 | Gln |
| Val | Leu | Pro | Asn<br>340 | Ser | Ser | Lys | Asp | Ser<br>345 | Ser | Gln | Pro | Ser | Cys<br>350 | Val | Glu |
| Gln | Ser | Thr<br>355 | Ser | Ser | Asp | Glu | Asn<br>360 | Glu | Met | Ser | Asp | Lys<br>365 | Ser | Lys | Lys |
| Gln | Cys<br>370 | Lys | Ser | Pro | Ser | Arg<br>375 | Arg | Asp | Ser | Tyr | Ser<br>380 | Asp | Ser | Ser | Gly |
| Ser<br>385 | Gly | Glu | Asp | Asp | Leu<br>390 | Val | Thr | Ala | Pro | Ala<br>395 | Asn | Ile | Ser | Asn | Ser<br>400 |
| Thr | Trp | Ser | Ser | Ala<br>405 | Leu | His | Gln | Thr | Leu<br>410 | Ser | Asn | Met | Val | Ser<br>415 | Gln |
| Ala | Gln | Ser | His | His<br>420 | Glu | Ala | Pro | Lys<br>425 | Ser | Gln | Glu | Asp | Thr<br>430 | Ile | Cys |
| Thr | Met | Phe | Tyr | Tyr | Pro | Gln | Lys | Ile | Pro | Asn | Lys | Pro | Glu | Phe | Glu |

|     |     |     |     | 435 |     |     |     | 440 |     |     |     | 445 |     |     |
| --- | --- | --- | --- | --- | --- | --- | --- | --- | --- | --- | --- | --- | --- | --- |
| Asp | Ser 450 | Asn | Pro | Ser | Pro | Leu 455 | Pro | Pro | Asp | Met | Ala 460 | Pro | Gly | Gln | Ser |
| Tyr 465 | Gln | Pro | Gln | Ser | Glu 470 | Ser | Ala | Ser | Ser 475 | Ser | Met | Asp | Lys | Tyr 480 |
| His | Ile | His | His | Ile 485 | Ser | Glu | Pro | Thr | Arg 490 | Gln | Glu | Asn | Trp | Thr 495 | Pro |
| Leu | Lys | Asn | Asp 500 | Leu | Glu | Asn | His | Leu 505 | Glu | Asp | Phe | Glu | Leu 510 | Glu | Val |
| Glu | Leu | Leu 515 | Ile | Thr | Leu | Ile | Lys 520 | Ser | Glu | Lys | Gly | Ser 525 | Leu | Gly | Phe |
| Thr | Val 530 | Thr | Lys | Gly | Asn | Gln 535 | Arg | Ile | Gly | Cys | Tyr 540 | Val | His | Asp | Val |
| Ile 545 | Gln | Asp | Pro | Ala | Lys 550 | Ser | Asp | Gly | Arg | Leu 555 | Lys | Pro | Gly | Asp | Arg 560 |
| Leu | Ile | Lys | Val | Asn 565 | Asp | Thr | Asp | Val | Thr 570 | Asn | Met | Thr | His | Thr 575 | Asp |
| Ala | Val | Asn | Leu 580 | Leu | Arg | Ala | Ala | Ser 585 | Lys | Thr | Val | Arg | Leu 590 | Val | Ile |
| Gly | Arg | Val 595 | Leu | Glu | Leu | Pro | Arg 600 | Ile | Pro | Met | Leu | Pro 605 | His | Leu | Leu |
| Pro | Asp 610 |

(2) INFORMATION FOR SEQ ID NO:2:

(i) SEQUENCE CHARACTERISTICS:
        (A) LENGTH: 1830 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

| | | | | | |
|---|---|---|---|---|---|
| CATGGCAGCC | CTTCCCCATC | TGTAATATCC | AAAGCCACCG | AGAAAGAGAC | TTTCACTGAT | 60 |
| AGTAACCAAA | GCAAAACTAA | AAAGCCAGGC | ATTTCTGATG | TAACTGATTA | CTCAGACCGT | 120 |
| GGAGATTCAG | ACATGGATGA | AGCCACTTAC | TCCAGCAGTC | AGGATCATCA | AACACCAAAA | 180 |
| CAGGAATCTT | CCTCTTCAGT | GAATACATCC | AACAAGATGA | ATTTTAAAAC | TTTTTCTTCA | 240 |
| TCACCTCCTA | AGCCTGGAGA | TATCTTTGAG | GTTGAACTGG | CTAAAAATGA | TAACAGCTTG | 300 |
| GGGATAAGTG | TCACGGTACT | GTTTGACAAG | GGAGGTGTGA | ATACGAGTGT | CAGACATGGT | 360 |
| GGCATTTATG | TGAAAGCTGT | TATTCCCCAG | GGAGCAGCAG | AGTCTGATGG | TAGAATTCAC | 420 |
| AAAGGTGATC | GCGTCCTAGC | TGTCAATGGA | GTTAGTCTAG | AAGGAGCCAC | CCATAAGCAA | 480 |
| GCTGTGGAAA | CACTGAGAAA | TACAGGACAG | GTGGTTCATC | TGTTATTAGA | AAAGGGACAA | 540 |
| TCTCCAACAT | CTAAAGAACA | TGTCCCGGTA | ACCCCACAGT | GTACCCTTTC | AGATCAGAAT | 600 |
| GCCCAAGGTC | AAGGCCCAGA | AAAAGTGAAG | AAAACAACTC | AGGTCAAAGA | CTACAGCTTT | 660 |
| GTCACTGAAG | AAAATACATT | TGAGGTAAAA | TTATTTAAAA | ATAGCTCAGG | TCTAGGATTC | 720 |
| AGTTTTTCTC | GAGAAGATAA | TCTTATACCG | GAGCAAATTA | ATGCCAGCAT | AGTAAGGGTT | 780 |
| AAAAAGCTCT | TTCCTGGACA | GCCAGCAGCA | GAAAGTGGAA | AAATTGATGT | AGGAGATGTT | 840 |
| ATCTTGAAAG | TGAATGGAGC | CTCTTTGAAA | GGACTATCTC | AGCAGGAAGT | CATATCTGCT | 900 |
| CTCAGGGGAA | CTGCTCCAGA | AGTATTCTTG | CTTCTCTGCA | GACCTCCACC | TGGTGTGCTA | 960 |

```
CCGGAAATTG  ATACTGCGCT  TTTGACCCCA  CTTCAGTCTC  CAGCACAAGT  ACTTCCAAAC    1020

AGCAGTAAAG  ACTCTTCTCA  GCCATCATGT  GTGGAGCAAA  GCACCAGCTC  AGATGAAAAT    1080

GAAATGTCAG  ACAAAAGCAA  AAACAGTGC   AAGTCCCCAT  CCAGAAGAGA  CAGTTACAGT    1140

GACAGCAGTG  GGAGTGGAGA  AGATGACTTA  GTGACAGCTC  CAGCAAACAT  ATCAAATTCG    1200

ACCTGGAGTT  CAGCTTTGCA  TCAGACTCTA  AGCAACATGG  TATCACAGGC  ACAGAGTCAT    1260

CATGAAGCAC  CCAAGAGTCA  AGAAGATACC  ATTTGTACCA  TGTTTTACTA  TCCTCAGAAA    1320

ATTCCCAATA  AACCAGAGTT  TGAGGACAGT  AATCCTTCCC  CTCTACCACC  GGATATGGCT    1380

CCTGGGCAGA  GTTATCAACC  CCAATCAGAA  TCTGCTTCCT  CTAGTTCGAT  GGATAAGTAT    1440

CATATACATC  ACATTTCTGA  ACCAACTAGA  CAAGAAAACT  GGACACCTTT  GAAAAATGAC    1500

TTGGAAAATC  ACCTTGAAGA  CTTTGAACTG  GAAGTAGAAC  TCCTCATTAC  CCTAATTAAA    1560

TCAGAAAAAG  GAAGCCTGGG  TTTTACAGTA  ACCAAAGGCA  ATCAGAGAAT  TGGTTGTTAT    1620

GTTCATGATG  TCATACAGGA  TCCAGCCAAA  AGTGATGGAA  GGCTAAAACC  TGGGGACCGG    1680

CTCATAAAGG  TTAATGATAC  AGATGTTACT  AATATGACTC  ATACAGATGC  AGTTAATCTG    1740

CTCCGGGCTG  CATCCAAAAC  AGTCAGATTA  GTTATTGGAC  GAGTTCTAGA  ATTACCCAGA    1800

ATACCCATGT  TGCCTCATTT  GCTACCGGAC                                        1830
```

( 2 ) INFORMATION FOR SEQ ID NO:3:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Ser  Leu  Gly  Ile  Ser  Val  Thr  Val  Leu  Phe  Asp  Lys  Gly  Gly  Val  Asn
1                   5                        10                       15

Thr  Ser  Val  Arg  His  Gly  Gly  Ile  Tyr  Val  Lys  Ala  Val  Ile  Pro  Gln
               20                       25                       30

Gly  Ala  Ala  Glu  Ser  Asp  Gly  Arg  Ile  His  Lys  Gly  Asp  Arg  Val  Leu
          35                       40                       45

Ala  Val  Asn  Gly  Val  Ser  Leu  Glu  Gly  Ala  Thr  His  Lys  Gln  Ala  Val
     50                       55                       60

Glu  Thr  Leu  Arg  Asn  Thr  Gly  Gln  Val  Thr  Asp  His  Tyr  Thr  Asn  Leu
65                       70                       75                       80

Leu  Gln  Tyr  Leu  Arg  Arg  Ala  Lys  Gln  Cys  Val  Asn  Asn  Ile  Ser  Ser
               85                       90                       95

His
```

( 2 ) INFORMATION FOR SEQ ID NO:4:

( i ) SEQUENCE CHARACTERISTICS:
        ( A ) LENGTH: 712 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
AGCTTGGGGA  TAAGTGTCAC  GGTACTGTTT  GACAAGGGAG  GTGTGAATAC  GAGTGTCAGA      60

CATGGTGGCA  TTTATGTGAA  AGCTGTTATT  CCCCAGGGAG  CAGCAGAGTC  TGATGGTAGA     120

ATTCACAAAG  GTGATCGCGT  CCTAGCTGTC  AATGGAGTTA  GTCTAGAAGG  AGCCACCCAT     180
```

```
AAGCAAGCTG  TGGAAACACT  GAGAAATACA  GGACAGGTAA  CAGATCATTA  TACCAACCTT      240

TTACAGTACC  TTAGAAGAGC  AAAACAATGT  GTGAATAACA  TCAGTTCTCA  TTGAGATCTC      300

TAAATTTGTC  AGCTAATCAA  GAAACCAAGC  CTGATATATA  TAACCATCTG  GGTTGTTGAT      360

TTTTCCTTCC  AAATTGAAAT  GCAAGTATTA  CAAGACATTT  TTTACTGAGG  AAGCTGACTT      420

TCTATGTCAC  ATTTAACGTT  ACATTACCAA  AGAGATCTGA  TGGGGGAGGG  ATGGAAATTG      480

CATTTTAAAT  TTGTTGTATA  AACATCTCAT  TTCTAGTGGT  TTTCACTCTT  ATTCTTTAGC      540

CTTAACACAA  AATTTATTTT  GTTGAAGTAC  ATTTTGAGTT  AGGGAGTTTA  ACCAAATTAT      600

CTATAATGGT  CTTTGGAGGA  AAAAGTTGTT  GTTTTGAGAC  AGGGTGTTGC  TGTGAGGCCC      660

AGGCTGGAGT  GCAGTGGCGC  AATCACGGCT  CACTGCAACC  TTGACTTCCC  AG             712
```

( 2 ) INFORMATION FOR SEQ ID NO:5:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Arg  Ala  Ala  Ile  Ser  Ala  Pro  Arg  Phe  Thr  Lys  Ala  Asn  Gly  Leu  Thr
 1               5                        10                       15

Ser  Met  Glu  Pro  Ser  Gly  Gln  Pro  Ala  Leu  Met  Pro  Lys  Asn  Ser  Phe
          20                       25                       30

Ser  Lys  Ala  Arg  Thr  Lys  Pro  Phe  Phe  Gln  Val  Ile  Ala  Ile  Phe  Asn
          35                       40                       45

Asn  Gln  Cys  Ala  Tyr  Val  Ser  Tyr  Gln  Ile  Asp  Phe  Ile  Ile  Lys  Cys
 50                       55                       60

Ser  Ser  Asp  Thr  Cys
 65
```

( 2 ) INFORMATION FOR SEQ ID NO:6:

( i ) SEQUENCE CHARACTERISTICS:
        ( A ) LENGTH: 258 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
AGAGCTGCCA  TTTCTGCGCC  CAGGTTCACC  AAAGCCAACG  GCCTAACCAG  CATGGAGCCT       60

TCTGGACAGC  CTGCACTCAT  GCCCAAGAAC  TCCTTCTCCA  AGGCAAGAAC  AAAACCTTTC      120

TTTCAAGTCA  TAGCCATTTT  TAATAACCAA  TGTGCTTATG  TGTCATACCA  AATAGATTTC      180

ATAATTAAAT  GCTCTTCAGA  CACATGCTAA  CAGTAGGACT  GCTCTGTGAT  GAACTAACAG      240

GTTTTGCTCA  CACTGCAG                                                      258
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TCGACCATGG CGGCCGCTCG AG 22

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TCGACTCGAG CGGCCGCCAT GG 22

( 2 ) INFORMATION FOR SEQ ID NO:9:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TCGACTGCTG TATATAAAAC CAGTGGTTAT ATGTACAGTA CTGCTGTATA TAAAACCAGT 60

GGTTATATGT ACAGTACG 78

( 2 ) INFORMATION FOR SEQ ID NO:10:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TCGACGTACT GTACATATAA CCACTGGTTT TATATACAGC AGTACTGTAC ATATAACCAC 60

TGGTTTTATA TACAGCAG 78

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGAATTCAAG AGAAAGGAAG TACAG 25

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

TGATCACTAG ACCAAGCTTT GGAT 24

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GGAATTCATG GCGCACGCTG GGAGAAC 27

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TGATCACTTC AGAGACAGCC AC 22

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GGAATTCAAA GGCTTTGCTT CGAAAG 26

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GTGATCACGC TTCTTTCTTT CCATG 25

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ATCCTCTTAG ACTGCGGCCG CTCA 24

( 2 ) INFORMATION FOR SEQ ID NO:18:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:18:

TGAGCGGCCG CAGTCTAAGA G  21

( 2 ) INFORMATION FOR SEQ ID NO:19:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:19:

GGTACCGAGC TCAATTGCGG  20

( 2 ) INFORMATION FOR SEQ ID NO:20:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:20:

Gly Leu Gly Phe
   1

( 2 ) INFORMATION FOR SEQ ID NO:21:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

Val Leu Phe Asp Lys
   1               5

( 2 ) INFORMATION FOR SEQ ID NO:22:

( i ) SEQUENCE CHARACTERISTICS:
      ( A ) LENGTH: 288 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:22:

CCTGGCTAAT TTTTATATTT TTAGTAGAGA TGGGGCCTCA CCATGTTGGC CAGGCTGGTC  60

TCCAACTTCT GACCTCAGGT GATCTGCCCA CCTTGGCCTC CCAAAGTGTT AGCCTTACCA  120

| | | | | | | |
|---|---|---|---|---|---|---|
| GCATGAGCCA | CTCCACCTGG | CCATTATCAT | ACATTTCTAA | CATGTATTAT | ATTTATAATA | 180 |
| GATTCTTTTT | AATCATTTAT | CTTTCTATAC | AGAAATGTAA | TAAAAACTTG | ATTTTGGAAC | 240 |
| TTTCAACCCC | TTGCTTTTGT | TCCTCTATTT | TTTTTTCCC | GGAATTCC | | 288 |

We claim:

1. A method of identifying an effective agent that alters the association of a Fas-associated protein (FAP) with Fas, comprising the steps of:
   a) contacting said FAP and Fas, under conditions that allow said FAP and FAS to associate, with an agent suspected of being able to alter the association of said FAP and Fas; and
   b) detecting the altered association of said FAP and Fas, wherein said altered association identifies an effective agent, and wherein said FAP interacts with the cytoplasmic domain of Fas.

2. The method of claim 1, wherein said altered association is detected by measuring the transcriptional activity of a reporter gene.

3. The method of claim 1, wherein said contacting is in vitro.

4. The method of claim 1, wherein said contacting is in vivo.

5. The method of claim 4, wherein said contacting is in a mammalian cell.

6. The method of claim 4, wherein said contacting is in a yeast cell.

7. The method of claim 1, wherein said FAP is a protein tyrosine phosphatase-BAS (PTP-BAS).

8. The method of claim 1, wherein said FAP is the 78,000 dalton glucose-regulated protein (GRP78).

9. The method of claim 1, wherein said effective agent is a drug.

10. The method of claim 1, wherein said effective agent is a protein.

11. The method of claim 10, wherein said protein is a PTP-BAS that lacks catalytic activity.

12. The method of claim 1, wherein said cytoplasmic domain of Fas comprises amino acids 321 to 335 of Fas.

* * * * *

UNITED STATES PATENT AND TRADEMARK OFFICE
CERTIFICATE OF CORRECTION

PATENT NO.   : 5,876,939
DATED        : March 2, 1999
INVENTOR(S)  : Reed et al.

It is certified that error appears in the above-identified patent and that said Letters Patent is hereby corrected as shown below:

Column 1,
Line 24, please delete "cytologic" and replace with -- cytotoxic --.

Column 3,
Line 27, please delete "lacz" and replace with -- lacZ --.

Column 7,
Line 38, please delete "cytologic" and replace with -- cytotoxic --.

Column 20,
Line 10, please delete "IL40" and replace with -- L40 --.

Column 21,
Line 2, please delete the space between the "C" and "G" in "(5'-TCGAC GTA".
Line 13, please delete *"cervisiae"* and replace with -- *cerevisiae* --.
Line 16, please delete "MATa" and replace with -- MATα --.
Line 59, please delete "TCA" and replace with -- TCA --.
Line 61, please delete "(5'-TGATCA" and replace with -- (5'-TGATCA --.
Line 64, please delete "(5'-TGATCA" and replace with -- (5'-TGATCA --.

Column 22,
Line 15, please delete "3)5'-GTGATCA" and replace with -- 3)5'-GTGATCA --.
Line 17, please delete "GTGATCA" and replace with -- GTGATCA --.
Line 39, please delete "-5'PO$_4$" and replace -- 3'PO$_4$ --.

UNITED STATES PATENT AND TRADEMARK OFFICE
CERTIFICATE OF CORRECTION

PATENT NO. : 5,876,939
DATED : March 2, 1999
INVENTOR(S) : Reed et al.

It is certified that error appears in the above-identified patent and that said Letters Patent is hereby corrected as shown below:

Column 23,
Line 56, please delete "pJGHeLa" and replace with -- pJG/HeLa --.

Signed and Sealed this

Twenty-second Day of January, 2002

Attest:

Attesting Officer

JAMES E. ROGAN
Director of the United States Patent and Trademark Office